(12) United States Patent
de Pablo et al.

(10) Patent No.: US 12,318,475 B2
(45) Date of Patent: Jun. 3, 2025

(54) INJECTABLE PASTES BASED ON OPPOSITELY CHARGED POLYMER/CALCIUM PHOSPHATE NANOPARTICLES

(71) Applicant: The University of Chicago, Chicago, IL (US)

(72) Inventors: Juan Jose de Pablo, Chicago, IL (US); Nader Taheri Qazvini, Chicago, IL (US); Monirosadat Sadati, Chicago, IL (US); Matthew Tirrell, Chicago, IL (US)

(73) Assignee: The University of Chicago, Chicago, IL (US)

( * ) Notice: Subject to any disclaimer, the term of this patent is extended or adjusted under 35 U.S.C. 154(b) by 887 days.

(21) Appl. No.: 16/084,864

(22) PCT Filed: Mar. 13, 2017

(86) PCT No.: PCT/US2017/022198
§ 371 (c)(1),
(2) Date: Sep. 13, 2018

(87) PCT Pub. No.: WO2017/209823
PCT Pub. Date: Dec. 7, 2017

(65) Prior Publication Data
US 2019/0054012 A1 Feb. 21, 2019

Related U.S. Application Data

(60) Provisional application No. 62/307,755, filed on Mar. 14, 2016.

(51) Int. Cl.
| | | |
|---|---|---|
| *A61K 9/00* | (2006.01) | |
| *A61K 9/06* | (2006.01) | |
| *A61K 9/51* | (2006.01) | |
| *A61K 35/32* | (2015.01) | |
| *A61K 38/18* | (2006.01) | |
| *A61L 27/12* | (2006.01) | |
| *A61L 27/16* | (2006.01) | |
| *A61L 27/36* | (2006.01) | |
| *A61L 27/54* | (2006.01) | |

(52) U.S. Cl.
CPC ............ *A61K 9/0019* (2013.01); *A61K 9/06* (2013.01); *A61K 9/5115* (2013.01); *A61K 9/5138* (2013.01); *A61K 35/32* (2013.01); *A61K 38/1875* (2013.01); *A61L 27/12* (2013.01); *A61L 27/16* (2013.01); *A61L 27/3608* (2013.01); *A61L 27/365* (2013.01); *A61L 27/54* (2013.01); *A61L 2300/414* (2013.01); *A61L 2400/06* (2013.01); *A61L 2400/12* (2013.01); *A61L 2430/02* (2013.01)

(58) Field of Classification Search
CPC .... A61L 27/12; A61L 27/3068; A61L 27/365; A61L 27/58; A61L 2430/02; A61L 2400/12; A61L 27/16; A61L 27/3608; A61L 27/54; A61L 2300/414; A61L 2400/06; A61K 9/0019; A61K 35/32; A61K 3/1875; A61K 9/06; A61K 9/5115; A61K 9/5138; A61K 38/1875
See application file for complete search history.

(56) References Cited

U.S. PATENT DOCUMENTS

| | | | |
|---|---|---|---|
| 5,336,264 A | 8/1994 | Constanz et al. | |
| 5,683,461 A | 11/1997 | Lee et al. | |
| 6,027,742 A | 2/2000 | Lee et al. | |
| 7,501,180 B2 | 3/2009 | Anderson et al. | |
| 7,514,249 B2 | 4/2009 | Gower et al. | |
| 7,544,496 B2 | 6/2009 | Gower et al. | |
| 7,547,449 B2 | 6/2009 | Gower et al. | |
| 7,820,191 B2 * | 10/2010 | Constantz .............. | A61K 6/853 623/23.62 |
| 8,168,170 B2 | 5/2012 | Myatt | |
| 8,309,134 B2 | 11/2012 | McDonough et al. | |
| 8,747,899 B2 | 6/2014 | Chaput et al. | |
| 8,889,196 B2 | 11/2014 | Xu | |
| 2004/0131562 A1 | 7/2004 | Gower et al. | |

(Continued)

FOREIGN PATENT DOCUMENTS

| | | |
|---|---|---|
| CN | 104860284 A * | 8/2015 |
| JP | 5158835 B2 | 3/2013 |

(Continued)

OTHER PUBLICATIONS

Dubey et al (Graphene: A versatile carbon-based material for bone tissue engineering), Hindawi Publishing Corporation, Stem cells international, vol. 2015, Article ID 804213, 12 pages. (Year: 2015).*

(Continued)

*Primary Examiner* — Mina Haghighatian
(74) *Attorney, Agent, or Firm* — Weaver Austin Villeneuve & Sampson LLP

(57) ABSTRACT

Provided herein are polymer-stabilized CaP nanoparticle formulations and related methods of manufacture. In certain embodiments, the methods reliably and selectively form nanoparticles with homogenous size, charge, and morphology. The CaP nanoparticles include calcium ions and phosphate ions with an ionic polymer, thereby forming stable hybrid nanoparticles. The CaP nanoparticle formulations include powders, suspensions and injectable pastes. According to various embodiments, the polymer-stabilized CaP nanoparticles may be polycation-stabilized (CaP/polymer (+) nanoparticles) or polyanion-stabilized (CaP/polymer(−) nanoparticles). The CaP/polymer nanoparticles can be freeze-dried and stored for months with no loss of properties or changes to their morphology.

14 Claims, 16 Drawing Sheets

(56) References Cited

U.S. PATENT DOCUMENTS

| | | | |
|---|---|---|---|
| 2005/0009176 A1* | 1/2005 | Constantz | A61K 6/838 |
| | | | 435/325 |
| 2005/0089579 A1* | 4/2005 | Li | A61P 19/08 |
| | | | 424/602 |
| 2005/0100559 A1 | 5/2005 | Myatt et al. | |
| 2007/0067882 A1 | 3/2007 | Atanasoska et al. | |
| 2008/0241256 A1 | 10/2008 | Kuhn | |
| 2009/0238947 A1 | 9/2009 | Flendrig et al. | |
| 2009/0263497 A1 | 10/2009 | Brito Lopes et al. | |
| 2010/0086618 A1 | 4/2010 | Pashley et al. | |
| 2011/0038921 A1 | 2/2011 | Wen et al. | |
| 2012/0039956 A1 | 2/2012 | Harel et al. | |
| 2013/0195921 A1 | 8/2013 | Bush | |
| 2014/0308332 A1 | 10/2014 | Lynch et al. | |
| 2015/0335577 A1 | 11/2015 | Agueros Bazo et al. | |

FOREIGN PATENT DOCUMENTS

| | | | |
|---|---|---|---|
| WO | WO-9111509 A1 | 8/1991 | |
| WO | WO2001041821 A1 | 6/2001 | |
| WO | WO2003095085 A1 | 11/2003 | |
| WO | WO-2005030257 A2 | 4/2005 | |
| WO | WO-2007079147 A2 | 7/2007 | |
| WO | WO-2017209823 A2 | 12/2017 | |

OTHER PUBLICATIONS

International Search Report and Written Opinion, dated Nov. 28, 2017, issued in PCT Application No. PCT/US17/22198.

Zhao, et al. "Calcium Phosphate Hybrid Nanoparticles: Self-Assembly Formation, Characterization, and Application as an Anticancer Drug Nanocarrier," Chem. Asian J., 2013, vol. 8, pp. 1306-1312.

Hood, et al. "Synthetic Strategies in the Preparation of Polymer/Inorganic Hybrid Nanoparticles," Materials, 2014, vol. 7, pp. 4057-4087.

Shkilnyy, et al., "Poly(ethylene imine)-Controlled Calcium Phosphate Mineralization," American Chemical Society, Langmuir, vol. 24, 2008, pp. 2102-2109.

Fukui, et al., "Bio-inspired nanoreactor based on a miniemulsion system to create organic-inorganic hybrid nanoparticles and nanofilms," J. Mater. Chem., 2012, 22, pp. 3493-3499.

Sharma, et al., "An insight into functionalized calcium based inorganic nanomaterials in biomedicine: Trends and transitions," Colloids and Surfaces B: Biointerfaces, No. 133, 2015, pp. 120-139.

Qazvini, et al. "Hybrid amorphous nanoparticles composed of calcium phosphate and a cationic polymer," Abstract of Symposium: Hybrid Polymers and Nanocomposites—Oral, 2 pages. Abstract as submitted for ACS Mar. 2016 meeting. Submission date of Oct. 12, 2015. Publication date unknown but after submission date.

Wang, et al., "Development of injectable organic/inorganic colloidal composite gels made of self-assembling gelatin nanospheres and calcium phosphate nanocrystals," Acta Biomaterialia, vol. 10, 2014, pp. 508-519.

EP Office Action dated Feb. 25, 2022, in Application No. EP18831200.3.

EP Search Report dated Mar. 11, 2021, in Application No. EP18831200.3.

International Preliminary Report on Patentability dated Jan. 23, 2020 in PCT/US2018/042063.

International Search Report and Written Opinion dated Sep. 14, 2018, issued in PCT/US2018/042063.

U.S. Restriction Requirement dated Jan. 25, 2022 in U.S. Appl. No. 16/630,816.

U.S. Non-Final Office Action dated May 27, 2022, in U.S. Appl. No. 16/630,816.

\* cited by examiner

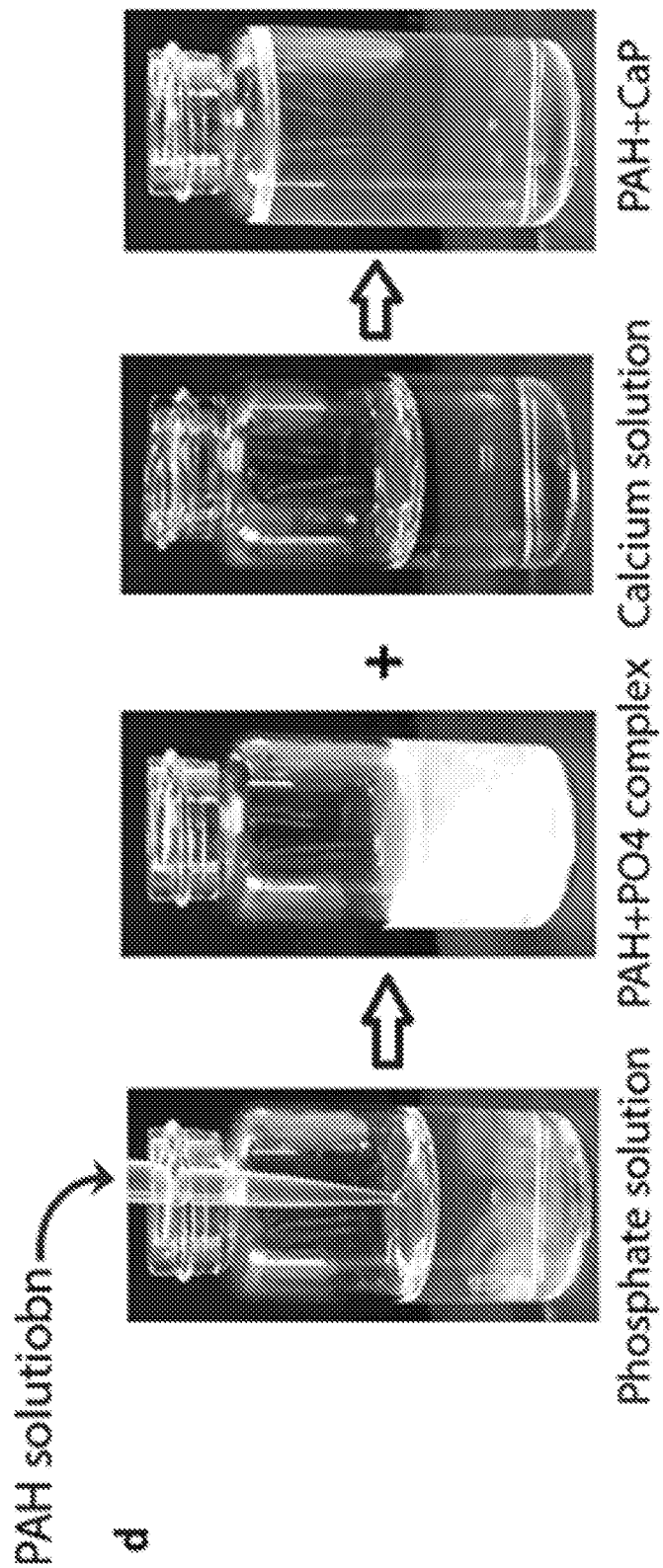
FIG 3, continued

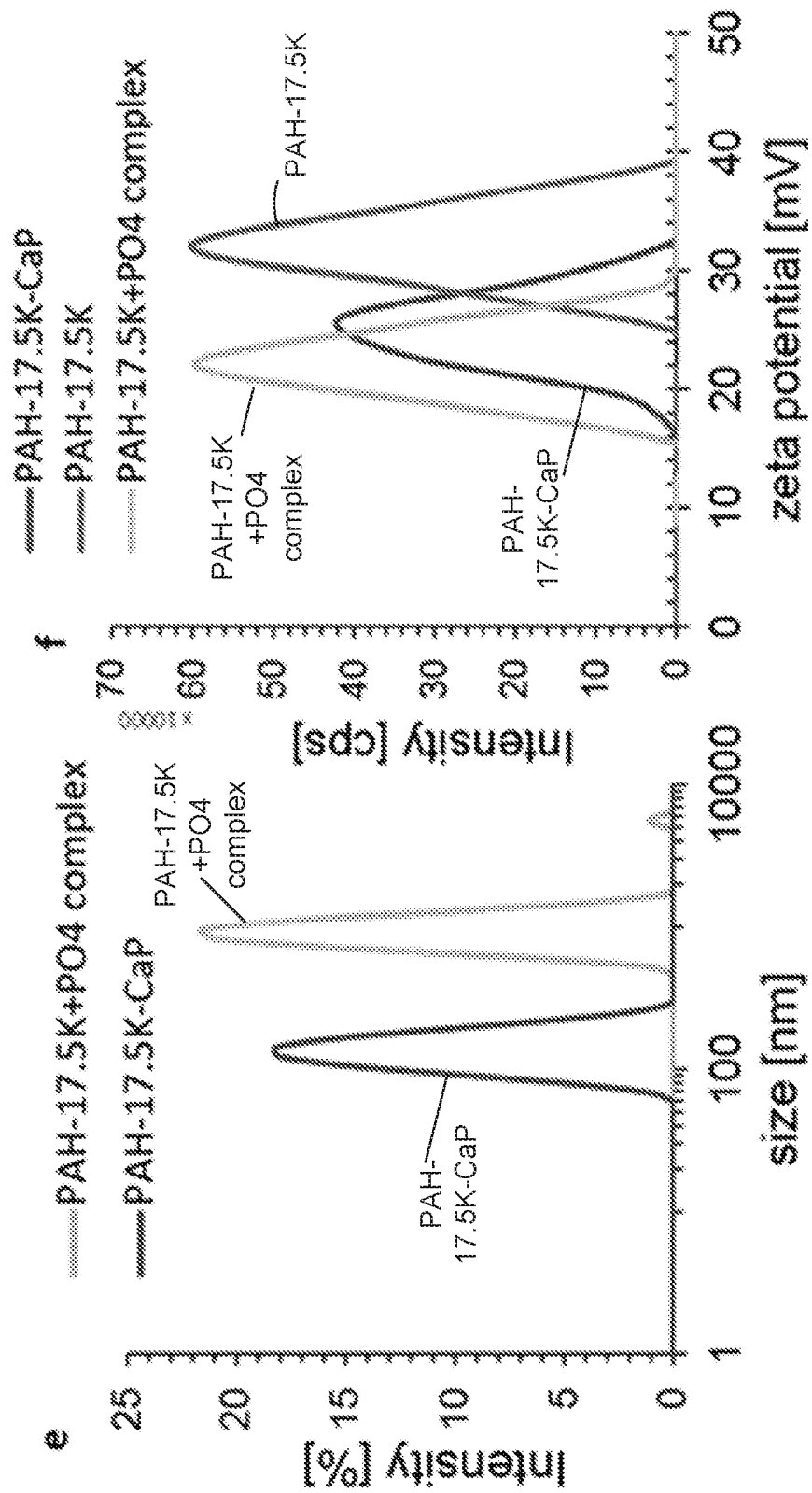
FIG 3, continued

INJECTABLE PASTES BASED ON OPPOSITELY CHARGED POLYMER/CALCIUM PHOSPHATE NANOPARTICLES

CROSS-REFERENCE TO RELATED APPLICATIONS

This application is a national application submitted under 35 U.S.C. § 371 of PCT Application No. PCT/US17/22198, filed Mar. 13, 2017, which claims priority to U.S. Provisional Application No. 62/307,755, filed Mar. 14, 2016, each of which is incorporated by reference herein and for all purposes.

STATEMENT OF GOVERNMENTAL SUPPORT

This invention was made with government support under grant number 70NANB 14H012 awarded by the National Institute of Standards and Technology, and grant number DMR1420709 awarded by the National Science Foundation, and grant number DE-AC02-06CH11357 awarded by the Department of Energy. The government has certain rights in the invention.

SUMMARY

One aspect of the disclosure relates to a nanoparticle including a calcium phosphate nanosphere and an organic polyelectrolyte. According to various implementations, the organic polyelectrolyte may be an organic polyanion or an organic polycation. In some implementations, the calcium phosphate nanosphere has a largest dimension of less than 50 nm. In some implementations, the calcium phosphate nanosphere has a largest dimension of less than 30 nm. In some implementations, the calcium phosphate nanosphere has a largest dimension of less than 20 nm. In some implementations, the calcium phosphate nanosphere is amorphous. In some implementations, the calcium phosphate nanosphere is between 25 wt % and 75 wt % of the nanoparticle and the organic polyelectrolyte is between 15 wt % and 65 wt % of the nanoparticle. The nanoparticle may further include water, e.g., about 5 wt % to 15 wt %. The nanoparticle may be part of an injectable paste. The injectable paste may further include one or more additional bioactive materials. Examples of organic polyelectrolytes include poly(aspartic acid), poly(acrylic acid), poly(acrylic acid sodium salt), poly(methacrylic acid) salts, poly(styrenesulfonic acid) salts, poly(2-acrylamido-2-methylpropane sulfonic acid), DNA, carboxymethyl cellulose, amelogenin, osteopontin, sulfonated dextran, poly(glutamic acid), poly(vinylphosphonic acid) and poly(vinyl sulphonic acid). Further examples include poly(allylamine hydrochloride), poly(allylamine), poly(ethyleneimine), poly(vinylpyridine) salts, poly(L-lysine), chitosan, gelatin, poly(diallyldimethylammonium chloride), and protamine. In some implementations, the nanoparticle is an organic polyanion and the nanoparticle is in a composition with a second nanoparticle that includes calcium phosphate nanosphere and an organic polycation.

Another aspect of the disclosure relates to compositions including a plurality of amorphous calcium phosphate nanospheres distributed within a polyelectrolyte matrix. In some implementations, the composition is lyophilized. The polyelectrolyte matrix may be a polyanion or a polycation matrix according to various implementations. In some implementations, the calcium phosphate nanospheres have an average largest dimension of less than 50 nm. In some implementations, the calcium phosphate nanospheres have an average largest dimension of less than 30 nm. In some implementations, the calcium phosphate nanospheres have an average largest dimension of less than 20 nm. In some implementations, the polyelectrolyte matrix includes at least one of poly(allylamine hydrochloride), poly(allylamine), poly(ethyleneimine), a poly(vinylpyridine) salt, poly(L-lysine), chitosan, gelatin, poly(diallyldimethylammonium chloride), and protamine. In some implementations, the polyelectrolyte matrix includes at least one of poly(aspartic acid), poly(acrylic acid), poly(acrylic acid sodium salt), poly(methacrylic acid) salts, poly(styrenesulfonic acid) salts, poly(2-acrylamido-2-methylpropane sulfonic acid), DNA, carboxymethyl cellulose, amelogenin, osteopontin, sulfonated dextran, poly(glutamic acid), poly(vinylphosphonic acid) and poly(vinyl sulphonic acid).

Another aspect of the disclosure relates to an injectable composition including a plurality of nanoparticles of an amorphous calcium phosphate nanosphere and a polyanion; and a plurality of a nanoparticles of an amorphous calcium phosphate nanosphere and a polycation. The injectable composition may further include a growth factor in some implementations. The injectable composition may further include a bone-derived material in some implementations. The injectable composition may further include one or more of a bone-morphogenic protein, osteocalcin, osteonectin, osteopontin, bone sialoprotein, decorin, and biglycan. The injectable composition may further include one or more of an anti-resorption agent, an anti-biotic agent, an anti-viral agent, an anti-tumor agent, and an immunosuppressive agent. In some implementations, the polyanion and polycation are present in substantially equivalent amounts by weight. In some implementations, the the nanoparticles of an amorphous calcium phosphate nanosphere and a polyanion and the nanoparticles of an amorphous calcium phosphate nanosphere and a polycation are present in substantially equivalent amounts by weight.

In some implementations, the composition further includes one or more bioactive components. Examples of bioactive components include graphene-based materials, silicate nanosheets, bioactive glasses, hydroxyapatite (HA), layered double hydroxides (LDHs) such as hydrotalcite and hydrocalumite (natural and synthetic), hexagonal boron nitride (hBN), graphitic carbon nitride (C3N4), transition metal oxides (TMOs) such as manganese dioxide (MnO2), titanium dioxide (TiO2), and transition metal dichalcogenides (TMDs) such as titanium disulfide (TiS2), molybdenum disulfide (MoS2), tungsten disulfide (WS2). In some implementations, the composition includes a graphene-based material and a silicate nanosheet.

Another aspect of the disclosure relates to a composition including a plurality of nanoparticles including calcium phosphate nanosphere and organic polyelectrolytes; a graphene-based material; and a silicate. In some implementations, the the composition is capable of recovering greater than 90% of initial elasticity after structural destruction.

In some implementations, the plurality of nanoparticles include nanoparticles of an amorphous calcium phosphate nanosphere and a polyanion and nanoparticles of an amorphous calcium phosphate nanosphere and a polycation. In some implementations, the composition is an injectable paste. In some implementations, the composition is in the form of a free-standing film. In some implementations, the composition is in the form of a 3D porous scaffold. In some implementations, the composition is a biocompatible coating. In some implementations, the composition further includes stem cells.

Another aspect of the disclosure relates to a composition including a plurality of nanoparticles including calcium phosphate nanosphere and organic polyelectrolytes, wherein the composition is in the form of a free-standing film or 3D porous scaffold.

Another aspect of the disclosure relates to a composition including a plurality of nanoparticles each including calcium phosphate nanosphere and an organic polyelectrolyte; and a bioactive material selected from a graphene-based material, a silicate nanosheet, a bioactive glasse, hydroxyapatite (HA), layered double hydroxides (LDHs), hexagonal boron nitride (hBN), graphitic carbon nitride (C3N4), a transition metal oxide and a transition metal dichalcogenide Another aspect of the disclosure relates methods of forming nanoparticles. In some embodiments, the methods involve mixing polyanion and calcium ion solutions together to form a mixture; and adding a phosphate ion solution to the mixture to form negatively charged polymer-stabilized calcium phosphate nanoparticles. In some embodiments, the methods involve mixing polycation and phosphate ion solutions together to form a mixture; and adding a calcium ion solution to the mixture to form positively charged polymer-stabilized calcium phosphate nanoparticles.

These and other aspects are discussed further with reference to the Figures.

BRIEF DESCRIPTION OF DRAWINGS

FIG. 5a is a transmission electron microscopy (TEM) micrograph showing a PAH/CaP nanoparticle prepared at 2x concentration: 10 mM $CaCl_2$, 5 mM $K_2HPO_4$ and 1000 μg/mL polymer. FIG. 5 is an close-up of a portion of FIG. 5a.

FIG. 5c shows synchrotron small-angle X-ray scattering profiles (log-log representation of scattering intensity versus scattering vector q) measured for freeze-dried polymer/CaP hybrid nanoparticles and the control sample prepared at 2x concentration.

FIG. 5d is a Kratky plot (I(q)×$q^2$ vs q) of the data in FIG. 5c.

DETAILED DESCRIPTION

Figure 1:
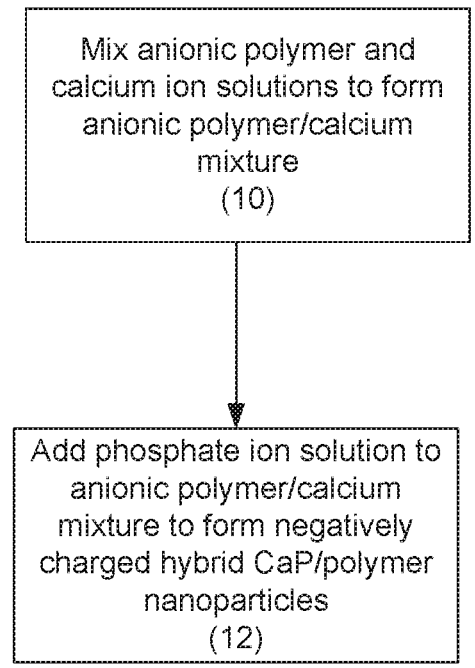
FIG. 1 shows an example of a method of forming hybrid CaP/polymer(−) nanoparticles.

Calcium phosphate (CaP)-based biomaterials are used in numerous applications including healing of bone defects, total joint replacement, orthopedics, dental fillings, and periodontal treatments, where they serve, for example, to enhance bone formation, fill bone voids, and deliver beneficial components to bone voids.

Provided herein are polymer-stabilized CaP nanoparticle formulations and related methods of manufacture. In certain embodiments, the methods reliably and selectively form nanoparticles with homogenous size, charge, and morphology. The CaP nanoparticles include calcium ions and phosphate ions with an ionic polymer, thereby forming stable hybrid nanoparticles. The CaP nanoparticle formulations include powders, suspensions and injectable pastes. According to various embodiments, the polymer-stabilized CaP nanoparticles may be polycation-stabilized (CaP/polymer$^{(+)}$ nanoparticles) or polyanion-stabilized (CaP/polymer$^{(-)}$ nanoparticles). The CaP/polymer nanoparticles can be freeze-dried and stored for months with no loss of properties or changes to their morphology.

The polymer-stabilized CaP nanoparticles may be referred to alternately as hybrid CaP/polymer nanoparticles or hybrid polymer/CaP nanoparticles. In some embodiments, the nanoparticles include amorphous CaP particles, which may be referred to as ACaP.

As used herein, the term "nanoparticle" refers to a particle, the largest dimension of which is less than 1 μm. The term "nanosphere" refers to a generally spherical particle, the largest dimension of which is less than 1 μm. Nanospheres are distinct from needle-like and other non-spherical formations, however it is understood that nanospheric particles disclosed herein may deviate from perfect spheres. It should be noted that although the below discussion refers chiefly to nanoparticles, in some embodiments, particles having sizes greater than 1 μm are provided.

The term "polyelectrolyte" refers to a polymer whose repeating units include an electrolyte group. Polyelectrolytes include polycations and polyanions. The term "amorphous" refers to a non-crystalline solid, having no regions of crystallinity. "Crystalline" refers to a relatively well-defined crystal structure.

As used herein the term "hybrid" refers to a composite material of an organic constituent and an inorganic constituent.

Also provided herein stable formulations including oppositely charged polymer-stabilized CaP nanoparticles, i.e., a formulation including CaP/polymer$^{(+)}$ and CaP/polymer$^{(-)}$. For example, in some embodiments, rehydrating a mixture of CaP/polymer$^{(+)}$ and CaP/polymer$^{(-)}$ powders or combining suspensions of CaP/polymer$^{(+)}$ with CaP/polymer$^{(-)}$, an injectable paste can be prepared with excellent control of rheological properties. In some embodiments, the formulations are neutral, containing approximately equal amounts of the cationic and anionic particles.

The size of amorphous CaP/polymer hybrid nanoparticles can be finely tuned in a range from 10 nm to 1 μm by controlling the polymer identity and composition, concentration, molecular weight, initial salt concentration, and mixing order. Unlike conventional methods, in certain embodiments, the methods disclosed herein can achieve control of nanoparticle size through initial salt concentration and work across a variety of mixing orders and preparation conditions. In one example, a phosphate ion solution at physiological conditions is combined with a polycation solution to form a suspension of phosphate/polymer aggregates. Subsequently, a calcium ion solution can be added to the phosphate/polymer complexes to yield CaP/polymer$^{(+)}$ nanoparticles. In another example, polyanion may be added to calcium to make a calcium/polymer complex, followed by addition of a phosphate solution to yield CaP/polymer$^{(-)}$ nanoparticles.

Depending on the physicochemical conditions of the synthesis and the concentrations of the salts and polymers used, the calcium phosphate may range from about 25 wt %-75 wt % and the polymer from about 15 wt %-65 wt %. The samples will typically include 5 wt %-10 wt % water.

In some embodiments, the methods disclosed herein permit control over the morphology of CaP/polymer nanoparticles. For example, the amorphous structure of CaP can be preserved in all formulations. This is significant because amorphous CaP has greater bioavailability than crystalline CaP. In some embodiments, the amorphous CaP nanoparticles are provided by controlling charge completely across polymer identity and composition, concentration, molecular weight, initial salt concentration, and mixing order. This is unlike conventional CaP nanoparticles, which deliver CaP in a crystalline state, especially at larger sizes (greater than 50 nm). The methods disclosed herein can prepare amorphous nanoparticles across a large size range, from 10 nm to greater than 1 μm.

As indicated above, oppositely charged CaP/polymer hybrid nanoparticles (i.e., CaP/polymer$^{(+)}$ and CaP/polymer$^{(-)}$) can be combined to form a neutral, stable, injectable formulation such as a paste or gel. The mechanical properties of this formulation may be controlled as described above (polymer identity and composition, concentration, molecular weight, initial salt concentration, and mixing order), enabling tunable control of rheological properties.

FIG. 1 shows an example of a method of forming hybrid CaP/polymer$^{(-)}$ nanoparticles. First, anionic polymer and calcium ion solutions are mixed to form an anionic polymer/calcium mixture. Block 10. Examples of anionic polymers include poly(aspartic acid), poly(acrylic acid), poly(acrylic acid sodium salt), poly(methacrylic acid) salts, poly(styrenesulfonic acid) salts, poly(2-acrylamido-2-methylpropane sulfonic acid), DNA, carboxymethyl cellulose, amelogenin, osteopontin, sulfonated dextran, poly(glutamic acid), poly(vinylphosphonic acid) and poly(vinyl sulphonic acid). Next a phosphate ion solution is added to the anionic polymer/calcium mixture. Block 12. This forms negatively charged hybrid CaP/polymer nanoparticles.

Figure 2:
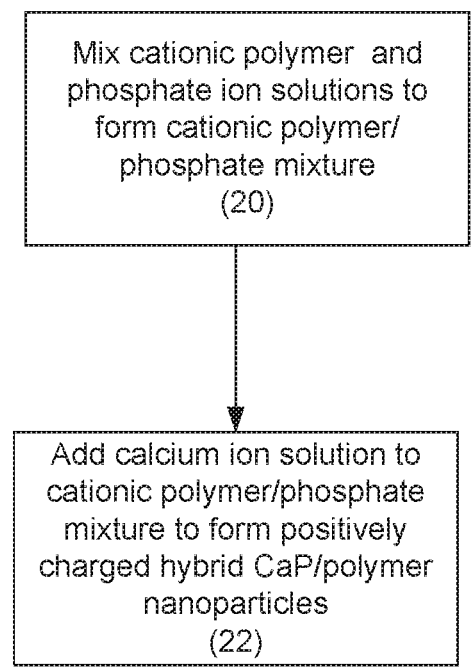
FIG. 2 shows an example of a method of forming hybrid CaP/polymer$^{(+)}$ nanoparticles.
Figure 3:
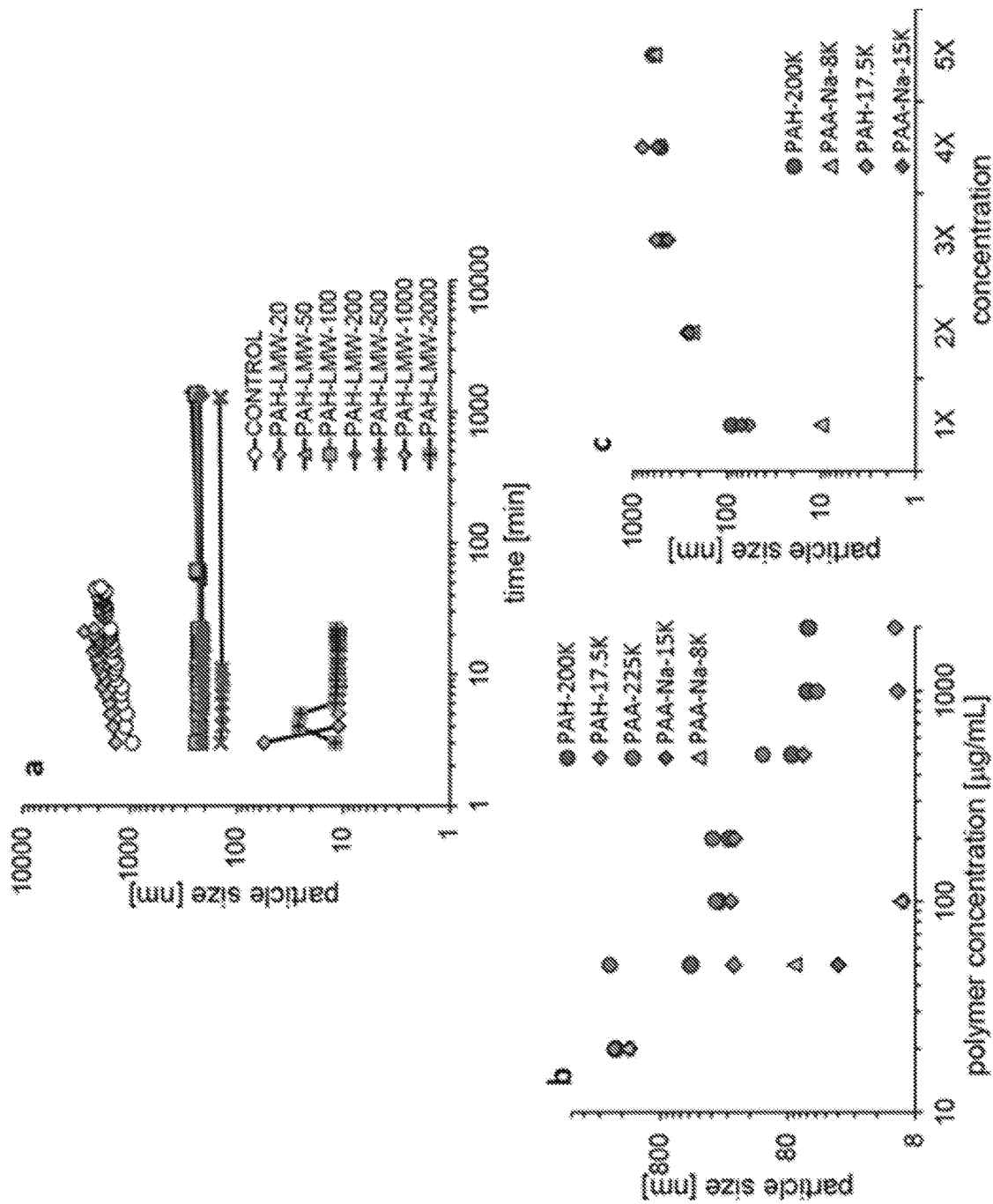
FIG. 3a shows the intensity averaged hydrodynamic radius of polymer/CaP hybrid particles in the presence of PAH-17.5 K ([PAH]=0-2000 μg/mL) versus time.
FIG. 3b is a graph showing the effect of polymer concentration on particle size.
FIG. 3c is a graph showing the effect of multiplying the solution concentrations at a constant polymer-to-ions ratio on the size of the particles.
FIG. 3d shows images of solutions during formation of PAH/CaP hybrid nanoparticles.
FIG. 3e shows dynamic light scattering (DLS) measurements of the solutions shown in FIG. 3d.
FIG. 3f shows zeta potential data measured for solutions containing only PAH, PAH/phosphate complexes, and PAH/CaP nanoparticles.
Figure 4:
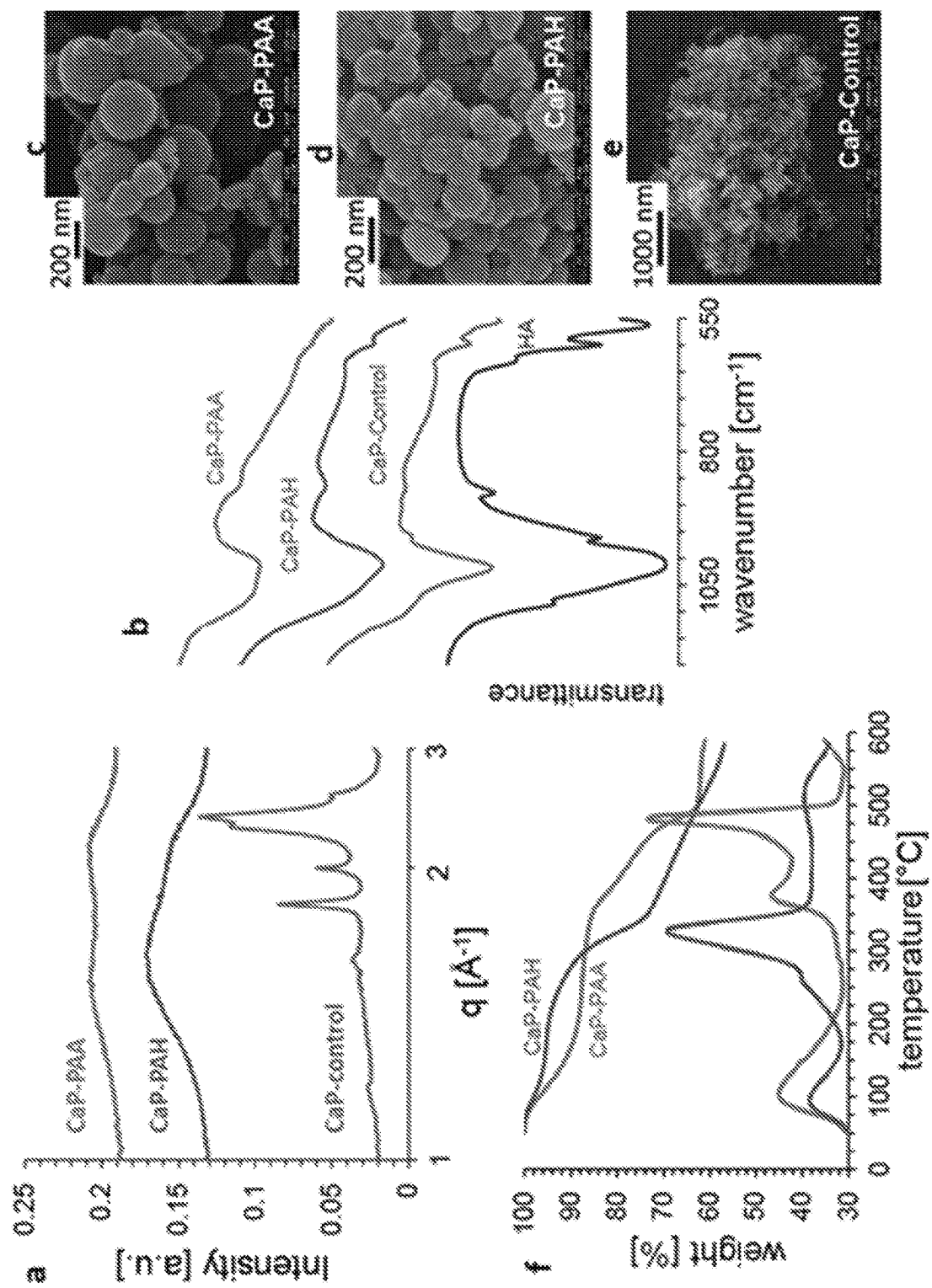
FIG. 4a shows synchrotron scattering profiles of CaP-PAH nanoparticles, CaP-PAA nanoparticles, and CaP control nanoparticles.
FIG. 4b shows Fourier transform infrared (FTIR) spectra of CaP-PAH nanoparticles and CaP-PAA nanoparticles.
FIGS. 4c and 4d show scanning electron microscopy (SEM) images of the hybrid CaP-polymer nanoparticles.
FIG. 4f shows a thermogravimetric analysis (TGA) of the polymer/CaP hybrid nanoparticles and the control sample prepared in the absence of polymer.
Figure 5:
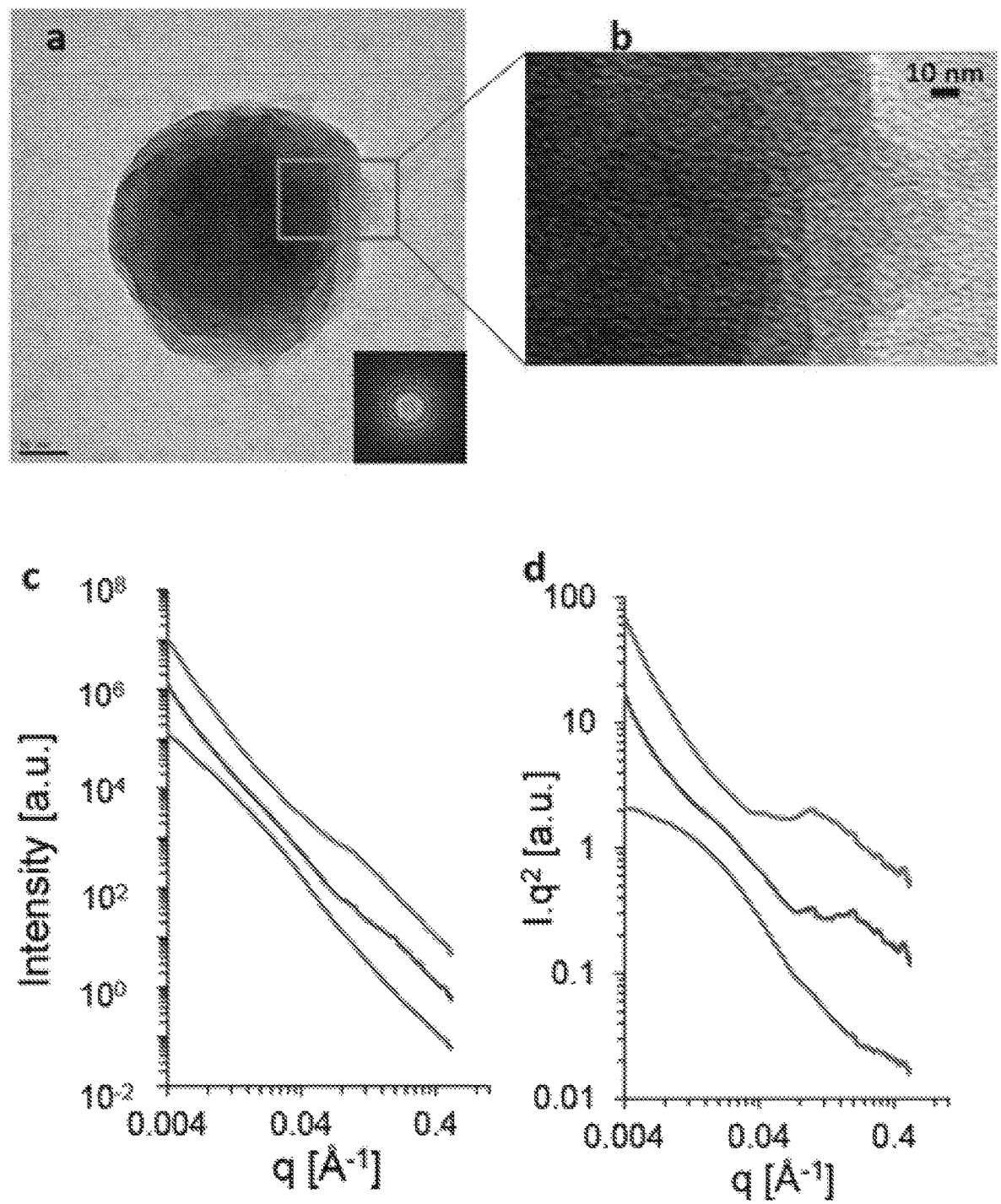
Figure 6:
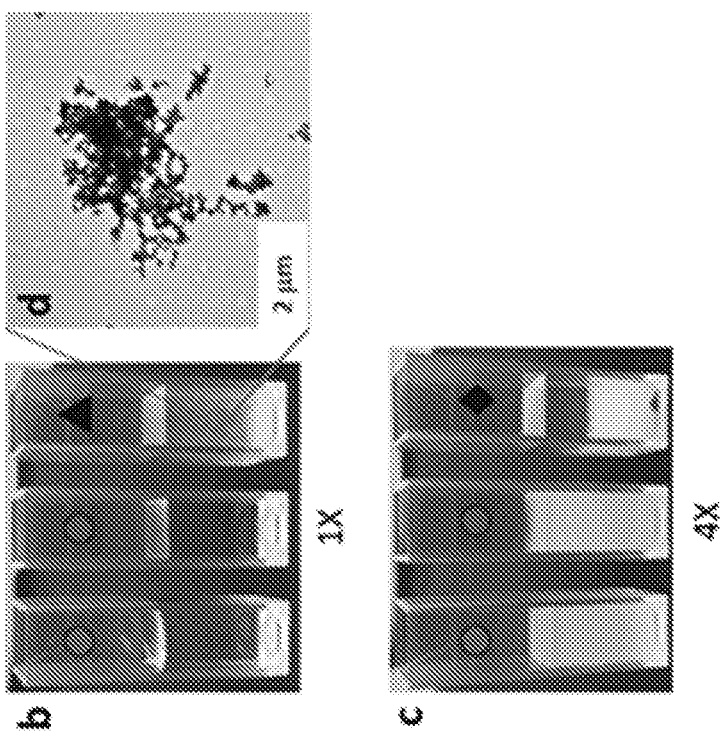
FIG. 6a is a graph of aggregate size as a function of time mixtures of as-prepared PAH/CaP and PAA/CaP dispersions synthesized at different concentrations (1x-5x).
FIGS. 6b and 6c are TEM images of as-prepared PAH/CaP and PAA/CaP synthesized at 1x concentration (FIG. 6b) and synthesized at 4x concentration (FIG. 6c).
FIG. 6d is a TEM image that shows the formation of cohesive aggregates several micrometers in size after mixing.
Figure 6:
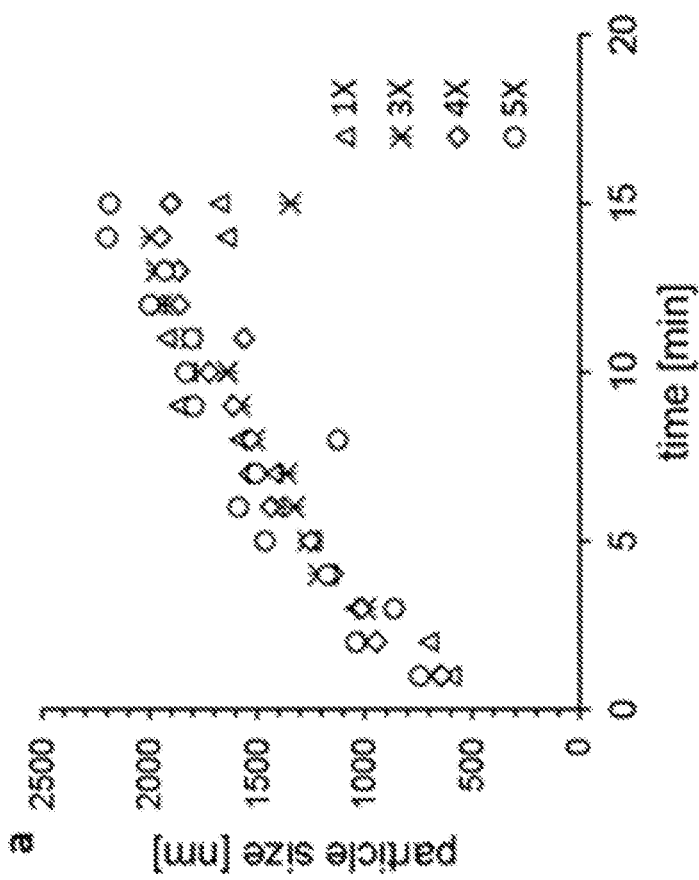
Figure 7:
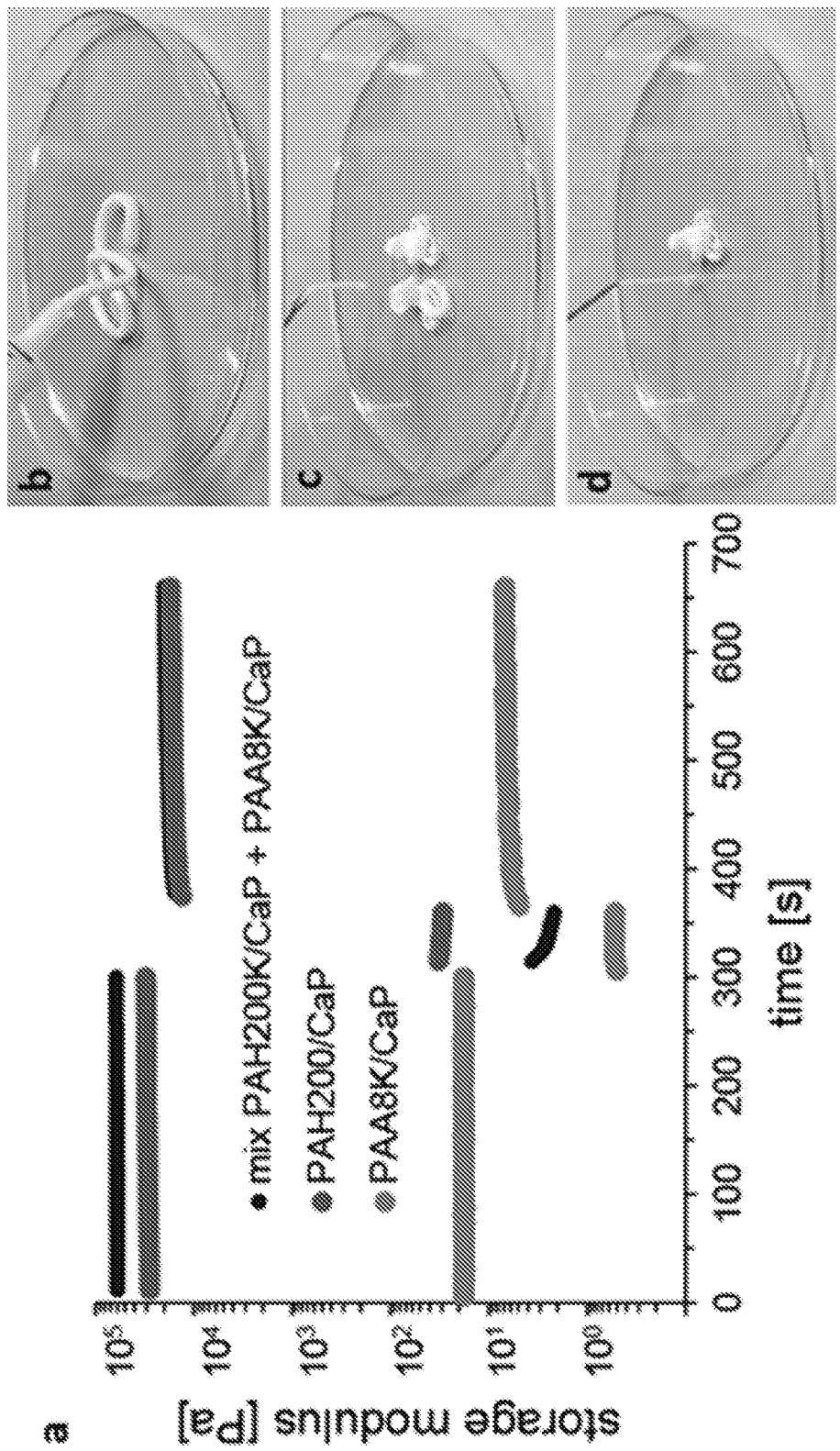
FIG. 7a shows the variation of the storage modulus G' as a function of time showing the structural recovery behavior of pastes made of PAA8/CaP, PAH200/CaP and a mixture of PAA8/CaP and PAH200/CaP hybrid nanoparticles after destruction by a 1000% oscillatory shear strain (solid content=20 w/v %).
FIGS. 7b-7d show images of continuous homogeneous threads of the viscoelastic paste injected through conventional medical syringes equipped with needles of different sizes.

FIG. 2 shows an example of a method of forming hybrid CaP/polymer$^{(+)}$ nanoparticles. First, cationic polymer and phosphate ion solutions are mixed to form a cationic polymer/phosphate mixture. Block 20. Examples of cationic polymers include poly(allylamine hydrochloride), poly(allylamine), poly(ethyleneimine), poly(vinylpyridine) salts, poly(L-lysine), chitosan, gelatin, poly(diallyldimethylammonium chloride), and protamine. Next a calcium ion solution is added to the cationic polymer/phosphate mixture. Block 22. This forms positively charged hybrid CaP/polymer nanoparticles.

The tunability of the size, charge, morphology, and rheological properties of the hybrid CaP/polymer nanoparticle compositions is described further below with respect to FIGS. 3-7.

First, FIGS. 3a-3f show results of analysis of the formation of as-synthesized polymer/CaP hybrid nanoparticles. CaP/polymer$^{(+)}$ and CaP/polymer$^{(-)}$ hybrid nanoparticles were synthesized according to the methods disclosed in FIGS. 1 and 2 and as described further below in the Examples using poly(allylamine hydrochloride) (PAH) and poly(acrylic acid) sodium salt (PAA), respectively.

To investigate how the PAA and PAH control the kinetics of nanoparticle formation, dynamic light scattering (DLS) was used to monitor the size (intensity averaged hydrodynamic radius) of the as-synthesized particles as a function of time and over a range of polymer concentration (0-2000 μg/mL) and salt concentration (5-25 mM $CaCl_2$ and 2.5-12.5 mM $K_2HPO_4$). The results are shown in FIGS. 3a-3c.

FIG. 3a shows the intensity averaged hydrodynamic radius of the polymer/CaP hybrid particles in the presence of PAH-17.5 K ([PAH]=0-2000 μg/mL) versus time. At [PAH]=50 and above, the size of the formed nanoparticles remains unchanged over 24 h. The concentrations of calcium and phosphate solutions were 5 and 2.5 mM, respectively. At salt concentrations of 5 mM $CaCl_2$ and 2.5 mM $K_2HPO_4$, in the absence of polymer, large aggregates in the form of apatite platelets formed and precipitated within 20 min. The same behavior was observed when a very low concentration of the polymer (20 μg/mL) was used. At higher polymer concentration, however, stable particles formed with a negligible size increase after 24 h.

FIG. 3b shows the effect of polymer concentration on size. Generally, smaller nanoparticles form at higher polymer concentration and, at the same polymer concentration, the nanoparticles that form in the presence of low molecular weight PAAs are smaller. For both polymers, the size of the particles decreased when the polymer concentration increased. For the systems containing highest polymer/ions ratios no precipitation occurred and these systems remained clear over several months. FIG. 3b shows that polymers with lower molecular weights formed smaller particles and particles containing PAA of lower molecular weight were smaller than particles prepared by PAH.

FIG. 3c shows the effect of multiplying the solution concentrations at a constant polymer-to-ions ratio on the size of the particles. 1× concentration: 5 mM $CaCl_2$, 2.5 mM $K_2HPO_4$ and 500 μg/mL polymer; 5× concentration: 25 mM $CaCl_2$, 12.5 mM $K_2HPO_4$ and 2500 μg/mL polymer. At a constant polymer-to-ions ratio, increasing the polymer and ions concentration considerably increased the size of the formed particles.

FIG. 3d shows images of solutions during formation of PAH/CaP hybrid nanoparticles. In this representative example, a polymer solution (here PAH) is added to a phosphate solution. The solution immediately became turbid indicating formation of highly hydrated polymer/phosphate complexes. After pouring the calcium solution into the PAH/phosphate complex the turbidity decreases considerably and stable hybrid nanoparticles form. This indicates that the formation of stable hybrid nanoparticles is mediated by counter-ion-induced phase separation.

The observations described with respect to FIG. 3d were quantified by DLS measurements shown in FIG. 3e. FIG. 3e shows that, in the case of PAH-stabilized particles, highly hydrated colloidal particles were formed by the complexation of PAH with phosphate ions. The average size of these complexes was about 900 nm, 1 min after addition of PAH solution to the phosphate solution. After addition of calcium solution, much smaller particles (about 100 nm) were formed which remained stable over months.

FIG. 3f shows zeta potential data measured for solutions containing only PAH, PAH/phosphate complexes, and PAH/CaP nanoparticles. The binding of phosphate ions to form phosphate-PAH highly hydrated complexes was confirmed by the decrease in the zeta potential of PAH after mixing with phosphate solution.

At pH 7.4, the amine groups on PAH are highly protonated and therefore the PAH molecules are expected to undergo microphase separation induced by phosphate ions. Depending on the concentration of polymer and salts, after addition of calcium ions, less turbid mixtures containing dehydrated calcium phosphate/polymer hybrid nanoparticles formed, as shown in FIG. 3d. The dehydration process is very rapid and can be ascertained by detection of smaller particle sizes after calcium ions were added, as shown in FIG. 3e. Moreover, detection of more positive zeta potential for the hybrid particles as shown in FIG. 3f can be considered a sign of calcium and phosphate ions reaction.

Returning to FIG. 3a, the concentration dependency and the constancy of the particle sizes over a long period of time (about 24 h) confirms the formation of calcium phosphate inside the polymer containing areas, i.e., hybrid nanoparticles. It can be inferred that PAH/phosphate complexation reduces the free phosphate ion concentration in the solution and therefore prevents mineralization of CaP apatite outside the particles. Furthermore, concentration independent, large negative or positive zeta potentials of the nanoparticles confirm that they are stabilized mainly due to the electrostatic repulsion effect. In summary, although there might be differences in particular mechanisms, both PAH and PAA can inhibit mineralization of CaP apatite in a concentration dependent manner and stimulate the formation of amorphous calcium phosphate inside the nanoparticles with high polymer concentration.

FIGS. 4a-4f demonstrate the structure and morphology of lyophilized samples of hybrid CaP nanoparticles. FIG. 4a shows synchrotron scattering profiles (using reciprocal d-spacing) of CaP-PAH nanoparticles, CaP-PAA nanoparticles, and CaP control nanoparticles (including commercial hydroxyapatite nanoparticles (Sigma-Aldrich)). While the control sample shows the distinct Bragg reflections of hydroxyapatite, the absence of any Bragg diffraction peaks in the hybrid nanoparticle samples clearly indicate that these samples are structurally amorphous and composed of amorphous CaP (ACaP).

FIG. 4b shows Fourier transform infrared (FTIR) spectra of CaP-PAH nanoparticles and CaP-PAA nanoparticles. Regardless of the polymer used, the FTIR spectrum has featureless and broadened phosphate bands at 900-1150 $cm^{-1}$ and at 565-605 $cm^{-1}$ which confirm the amorphous structure of the hybrid CaP-polymer nanoparticles. For comparison, the FTIR spectrum of the CaP control nanoparticles is also shown.

FIGS. 4c and 4d show scanning electron microscopy (SEM) images of the hybrid CaP-polymer nanoparticles. The images confirm that the hybrid CaP-polymer nanoparticles are submicron-sized spherical particles. FIG. 4e shows an SEM image of the CaP control nanoparticles for comparison. Unlike the hybrid polymer/CaP nanoparticles, the control sample is in the form of densely aggregated needle-like crystals. The average size of the hybrid polymer/ACaP nanoparticles are in a good agreement with the DLS results confirming the dehydration during formation of these hybrid nanoparticles FIG. 4f shows a thermogravimetric analysis (TGA) of the polymer/CaP hybrid nanoparticles and the control sample prepared in the absence of polymer. FIG. 4f also shows the first derivatives of the TGA curves. The composition of the hybrid nanoparticles was further assessed by the TGA, which shows that a significant amount of polymer has been incorporated into the particles. Quantitatively, the TGA analysis shows that the particles are about 35-40 wt % of polymer, 50-55 wt % of ACaP, and water. The weight loss up to 200° C. is attributed to dehydration. The weight losses at 330-600° C. and 375-600° C. are due to degradation of PAH and PAA, respectively. Compared to the decomposition profile of pure PAH and PAA, it can be concluded that complexation of the polymers with calcium or phosphate ions has increased the thermal stability of the polymers.

The internal structures of the freeze-dried particles were evaluated using transmission electron microscopy (TEM). TEM analysis reveals the presence of the small CaP spheres with a size of 3-6 nm inside the particles with a higher population near the center. FIG. 5a is a TEM micrograph showing a PAH/CaP nanoparticle prepared at 2× concentration: 10 mM $CaCl_2$, 5 mM $K_2HPO_4$ and 1000 μg/mL polymer. The fast Fourier transform (inset) of the high-resolution image in FIG. 5a confirms that these nanospheres are non-crystalline in nature. (Imaging at higher magnification was not possible because of the structural instabilities in the samples by electron, which was revealed by the formation of voids on the particle surfaces.) Overall, the TEM analysis suggests that both the PAA/CaP and PAH/CaP particles are amorphous structures of ACaP nanospheres dispersed in a polymer matrix.

FIG. 5c shows synchrotron small-angle X-ray scattering profiles (log-log representation of scattering intensity versus scattering vector q) measured for freeze-dried polymer/CaP hybrid nanoparticles and the control sample prepared at 2× concentration. FIG. 5c shows a representation of the scattering data by Kratky plot ($I \times q^2$ versus q). The high q features in the profiles of the hybrid nanoparticles signify structural complexity at the length scale of a few nanometers.

The shape of SAXS pattern depends on the particles shape and their local arrangement, although the presence of any scattering substructure might complicate the SAXS pattern. The control sample shows a scattering profile of aggregated hydroxyapatite platelets. The polymer stabilized particles, however, exhibit a SAXS pattern with three characteristic regions. At the low-q region, the signal is controlled by the overall shape of the particle. The slope in this region decreases as $q^{-4}$ indicative of scattering from aggregates of spherical particles with smooth interfaces. At intermediate q values (0.01-0.06 Å$^{-1}$) a small feature is observed for both samples, although at slightly different q values. These features are better shown when the data are plotted on a Kratky plot ($I(q) \times q^2$ vs q) as in FIG. 5d and can be ascribed to a characteristic length scale resulted from nanoparticles of smaller size or the mean spacing of calcium phosphate nanospheres present inside the particles. Another prominence at high q values, about 0.08-0.3 Å$^{-1}$ can be observed for both samples. These features can be attributed to the presence of CaP nanoparticles with size of about 3-6 nm dispersed in polymer matrix. The SAXS results confirm the morphological feature inferred from TEM analysis, in which the PAH/CaP and PAA/CaP particles can be considered as hybrid composites composed of amorphous calcium phosphate nanospheres dispersed in a polymer matrix. Interestingly, the projected internal structure is reminiscent of the internal structure of casein micelles in which colloidal calcium phosphate nanoclusters are proposed to be dispersed in a matrix of casein proteins.

The tunable size and surface charge of the hybrid particles make them promising for various applications. In some embodiments, injectable gels based on self-assembly of the polymer/ACaP hybrid nanoparticles are provided. The electrostatic self-assembly between the oppositely charged hybrid particles results in a cohesive paste that is suitable for injection. FIGS. 6a-6d demonstrate the aggregation behavior of the oppositely charged polymer/CaP hybrid nanoparticles by electrostatic self-assembly. In particular, DLS measurements and TEM analysis demonstrate formation of the large aggregates were detected after mixing dilute dispersions of the oppositely charged hybrid nanoparticles. FIG. 6a is a graph of the size of the aggregates as a function of time mixtures of as-prepared PAH/CaP and PAA/CaP dispersions synthesized at different concentrations (1×-5×). All samples were diluted to a solid content of about 0.03 w/v %. Regardless of the size of the particles that were mixed, the size of the formed aggregates was the same and increased linearly in time. FIGS. 6b and 6c are TEM images of as-prepared PAH/CaP and PAA/CaP synthesized at 1× concentration (FIG. 6b) and synthesized at 4× concentration (FIG. 6c). The leftmost solution in FIGS. 6b and 6c is PAA/CaP, the middle solution in FIGS. 6b and 6c is PAA/CaP, and the rightmost solution is the combined PAH/CaP and PAA/CaP. After 1-2 h of equilibration, the aggregates precipitated and a two-phase system was formed (rightmost solution in FIGS. 6b and 6c). TEM analysis also confirmed the formation of cohesive aggregates several micrometers in size after mixing (FIG. 6d).

The viscoelastic properties of the pastes prepared by mixing of 20 wt % dispersions of oppositely charged hybrid nanoparticles were investigated by low amplitude oscillatory rheometry within the linear viscoelastic region. The linear viscoelastic region was detected by oscillatory strain sweeps. Oscillatory time sweep measurements were used to measure the storage modulus G' and loss modulus G". Indeed, the binary mixture of oppositely charged hybrid nanoparticles showed solid-like behavior as verified by the larger storage modulus than the loss modulus, i.e. tan δ<1. Furthermore, the viscoelastic properties of the dispersions of similarly charged hybrid nanoparticles were strongly influenced by the molecular weight of the polymer used. However, at the same solid concentration the G' value of the binary mixtures was always higher than that of systems containing similarly charged hybrid nanoparticles. This is the case for all samples including polymers of different molecular weights and can be considered as another indication for the formation of electrostatic attractions between the building blocks of the paste, i.e. oppositely charged hybrid nanoparticles. As the pastes are made up of the electrostatically bound PAA/CaP and PAH/CaP hybrid particles, a structural recovery can be expected for these materials.

The structural recovery after structural destruction at high oscillatory strain amplitudes (1000%) was measured by a simple rheological test, with the results shown in FIGS. 7a-7d. FIG. 7a shows the variation of G' as a function of time showing the structural recovery behavior of pastes made of PAA8/CaP, PAH200/CaP and a mixture of PAA8/CaP and PAH200/CaP hybrid nanoparticles after destruction by a 1000% oscillatory shear strain (solid content=20 w/v %). The immediate result of high oscillatory strain (1000% for 1 min, $t_{ON}$=300 s, $t_{OFF}$=360 s) was complete structural disruption evidenced by transformation of the pastes into a liquid-like material. Right after cessation of destructive strain (t=360 s), all pastes exhibited solid gel responses, with values of immediately restored G' of with values of ~15000 Pa. At t=660 s (5 min after destruction), the values of recovered G' for the paste were ~30% that of the original moduli prior to fracture (FIG. 7a). Although, the ultimate storage modulus of the paste is clearly lower than the preshear values, its elasticity is still considerable and reaches to about 20000 Pa. This means that the pastes have rapid self-healing capabilities and can be easily processed as low viscosity materials, for example in minimally invasive approaches, and subsequently form an elastic paste. This rapid recovery property can prevent the paste from flowing and being washed out after injection to a bone defect.

FIGS. 7b-7d show images of continuous homogeneous threads of the viscoelastic paste injected through conventional medical syringes equipped with needles of different sizes. Interestingly, the paste can preserve its thread-like structure after injection into an aqueous solution. The filter-pressing phenomenon, a common problem related to injectable calcium phosphate formulations, was only observed when the pastes were made of nanoparticles with sizes smaller than 60 nm mainly because of very strong interactions between the oppositely charged nanoparticles.

According to various embodiments, the injectable formulations may be self-setting or non-setting formulations. The injectable compositions may include additional components with examples including, but not limited to, osteo-inductive agents, bone-derived materials (e.g., demineralized bone powder), therapeutic agents, and other components suitable for a particular application. For example, the injectable composition may include one or more growth factors, or one or more bone-morphogenic proteins and other proteins such as osteocalcin, osteonectin, osteopontin, bone sialoprotein, decorin, and biglycan.

Examples of growth factors include insulin growth factor (IGF), transforming growth factor-β (TGF-β), osteoinductive factor (GIF), basic fibroblast growth factor (bFGF), acidic fibroblast growth factor (aFGF), epidermal growth factor (EGF), vascular endothelial growth factor) (VEGF), growth and differentiation factor (GDF) and platelet-derived growth factor (PDGF).

The composition may further include one or more agents such as anti-resorption agents, antibiotic agents, antiviral agents, antitumor agents, and immunosuppressive agents.

Figure 8A:
FIG. 8a shows an image of paste including a mixture) of polymer/ACaP hybrid nanoparticles, silicate nanosheets (SNs), and graphene oxide (GO) being dispensed.

In some embodiments, the polymer/ACaP hybrid nanoparticles can be mixed with other biocompatible charged nanoparticles to prepare new viscoelastic materials. These materials can be easily processed into multifunctional macrostructures including free-standing films, biocompatible coatings, ready-to-use injectable pastes, and 3D porous scaffolds. For example, a mixture (10 w/v % in water) of polymer/ACaP hybrid nanoparticles, silicate nanosheets (SNs), and graphene oxide (GO) results in an injectable paste. FIG. 8a shows an image of the paste being dispensed. An example synthesis is described below in Example 3.

Figure 8B:
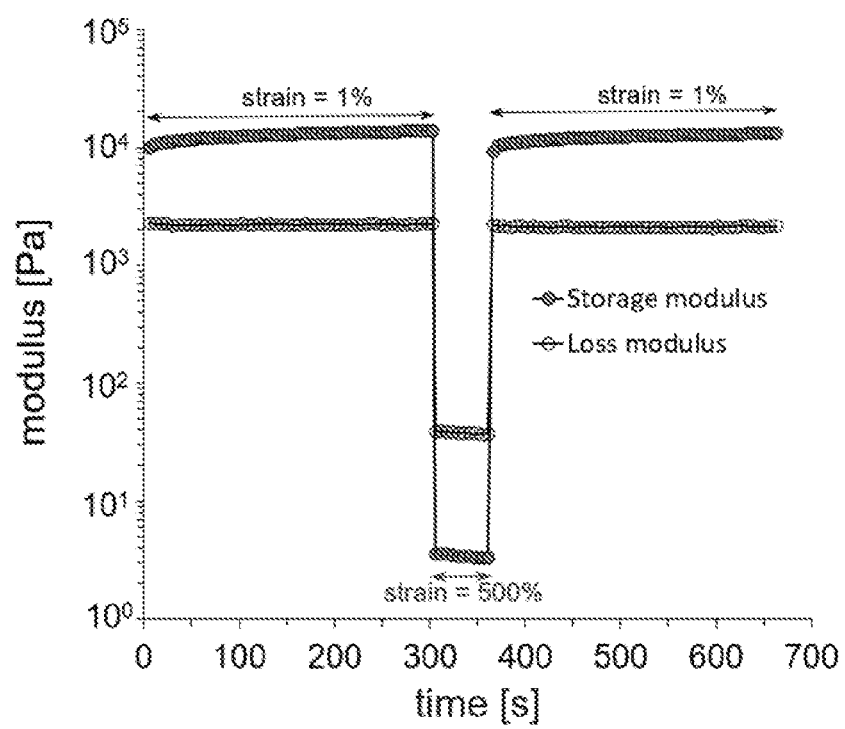
FIG. 8b shows variation of storage and loss moduli as a function of time of a paste (composition: PAH/CaP:PAA/CaP:SNs:GO 50:50:100:2; solid content=10 w/v %) after destruction by a 500% oscillatory shear strain.

FIG. 8b shows variation of storage and loss moduli as a function of time of a paste (composition: PAH/CaP:PAA/CaP:SNs:GO 50:50:100:2; solid content=10 w/v %) after destruction by a 500% oscillatory shear strain. The structural recovery behavior of the pastes is shown in FIG. 8b. These pastes show a better capability for recovery of initial viscoelastic properties compared to the system made up of electrostatically bound PAA/CaP and PAH/CaP hybrid nanoparticles without the SN and GO components. As seen in FIG. 8b, within 5 min after complete structural destruction, almost 95% of initial elasticity was recovered, verifying remarkable self-healing performance of the multi-component paste.

Moreover, by molding and freeze-drying injectable hybrid systems of polymer/ACaP hybrid nanoparticles, SN, and GO, free-standing structures in the form of 3D porous scaffolds can be prepared. Experiments show that these hybrid structures are biocompatible and promote in vitro osteogenic differentiation of a variety of mesenchymal stem cells in the absence of osteoinductive factors or boost the potency of bone morphogenetic proteins (BMPs) in inducing stem cell osteogenesis. For example, immortalized Mouse Adipose-Derived (iMAD) and immortalized Mouse Embryo Fibroblast (iMEF) mesenchymal stem cells (MSC) cultured on the porous scaffolds remained viable and showed a long-term proliferation and osteogenic differentiation without any osteogenic inducers, as confirmed by optical microscopy (FIG. 9a) and scanning electron microscopy (SEM) (FIG. 9b). The iMAD and iMEF mesenchymal stem cell lines were infected with Adenovirus Containing Green Fluorescent Protein (Ad-GFP), seeded on the surface of the scaffold and maintained in complete Dulbecco's Modified Eagle Medium (DMEM), containing 10% (v/v) fetal bovine serum (FBS), 100 U ml$^{-1}$ penicillin and 100 μg/ml streptomycin at 37° C. in 5% $CO_2$.

Figure 9A:
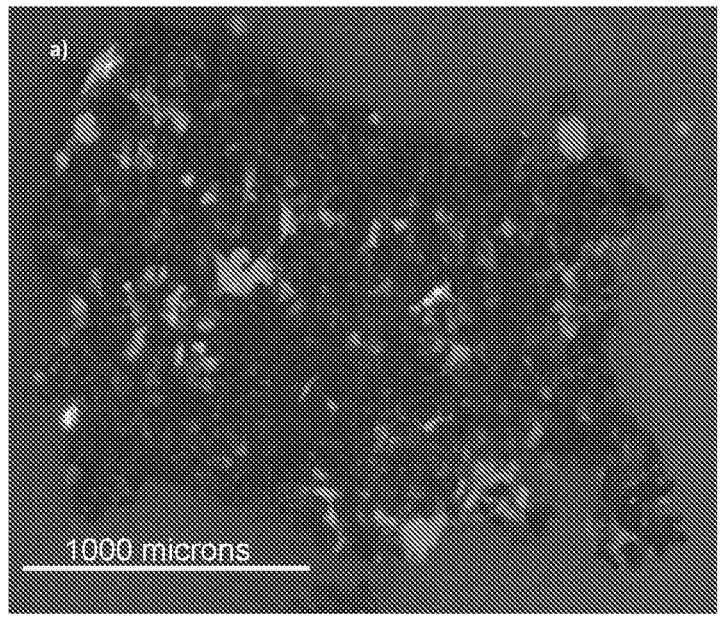
FIG. 9a an optical microscopy image of iMAD mesenchymal stem cells on PAH-CaP/PAA-CaP/SNs/GO hybrid scaffolds
Figure 9B:
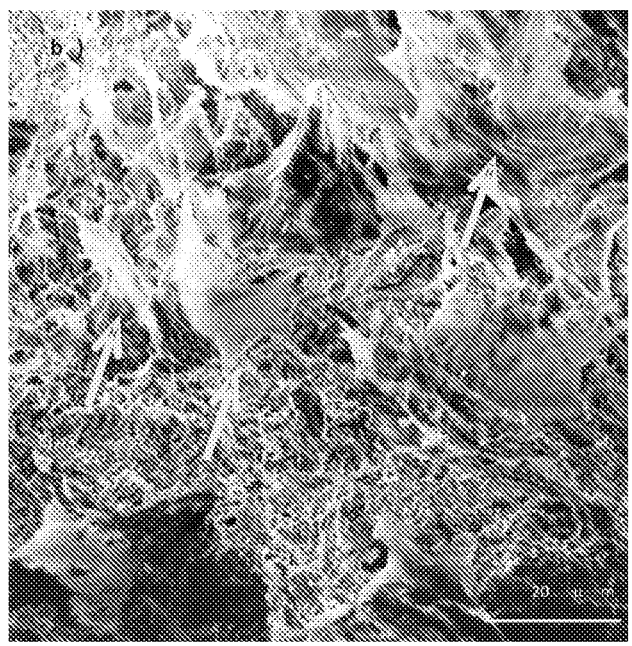
FIG. 9b is an SEM image showing morphology and interaction of the stem cells with the hybrid scaffold.

FIG. 9a an optical microscopy image of iMAD mesenchymal stem cells on PAH-CaP/PAA-CaP/SNs/GO hybrid scaffolds. Optical microscopy images revealed a homogeneous attachment and viability of cells on the scaffold at day 3. FIG. 9b is an SEM image showing morphology and interaction of the stem cells with the hybrid scaffold. Cells were fixed at day 7 for SEM imaging. Arrows indicate some of the MSCs.

Moreover, SEM images showed cells with elongated morphology and with several long protrusions stretched out from the cell body.

This is one example of a multi-component system based on the self-assembly of three bioactive nanomaterials (ACaP, GO, and silicate nanosheets) into macrostructures for bone tissue engineering. The ACaP nanoparticles are expected to be easily resorbed in vivo and provide calcium and phosphate ions required for fast bone regeneration. Moreover, in aqueous solution, silicates nanosheets can dissociate into $Na^+$, $Li^-$, $Mg^{2+}$ ions and $Si(OH)_4$ with a positive impact on cells behavior. The high elastic modulus of graphene materials is also believed to be a driving force for osteogenic differentiation. Therefore, these methods and materials can be adjusted to create new hybrid functional materials based on a spectrum of bioactive nanomaterials that could synergistically direct the differentiation of stem cells toward osteogenic lineage.

Further discussion of graphene and silicate nanosheet materials that may be used in the multi-component systems is below in Example 4. Further example of bioactive materials that may be used in multi-component systems that include calcium phophate/polymer hybrid nanoparticles include bioactive glasses, hydroxyapatite (HA), layered double hydroxides (LDHs) such as hydrotalcite and hydrocalumite (natural and synthetic), hexagonal boron nitride (hBN), graphitic carbon nitride ($C_3N_4$), transition metal oxides (TMOs) such as manganese dioxide ($MnO_2$), titanium dioxide ($TiO_2$), and transition metal dichalcogenides (TMDs) such as titanium disulfide ($TiS_2$), molybdenum disulfide ($MoS_2$), tungsten disulfide ($WS_2$).

EXAMPLES

Example 1

Preparation of Hybrid Nanoparticles and Injectable Compositions

Amorphous hybrid nanoparticles were synthesized by first mixing the poly(acrylic acid) sodium salt (PAA) and $CaCl_2$ solutions and then pouring a $K_2HPO_4$ solution into the PAA/$CaCl_2$ mixture at room temperature and at pH=7.4. In the case of positively charged nanoparticles, the mixing order was inverse, i.e., the $CaCl_2$ solution was poured into a premixed poly(allylamine hydrochloride) (PAH) and $K_2HPO_4$ solution. Except for the system prepared at the lowest concentration, the particles were collected immediately by centrifugation and stored at −80° C. before lyophilization at −4° C. At the selected working conditions, each polymer exhibited a net similar charge on the formed hybrid nanoparticles. Details of the syntheses are provided below Materials: Poly(acrylic acid) sodium salt (PAA, MW=7000 g/mol, 15000 g/mol and 225000 g/mol), poly(allylamine hydrochloride) (PAH, MW=17500 g/mol), calcium chloride dihydrate ($CaCl_2 \cdot 2H_2O$), and potassium phosphate dibasic ($K_2HPO_4$) were purchased from Sigma-Aldrich. PAH (MW~200000 g/mol) was purchased from Alfa-Aeser.

Preparation of hybrid nanoparticles: Stock solutions of PAA (30 mg/mL), PAH (30 mg/mL), calcium (1 M) and phosphate (0.5 M) were prepared in Tris-buffered saline (TBS 1×) and the pH was adjusted to 7.4. The negatively charged hybrid nanoparticles were prepared by first mixing of PAA stock solution (v=0.167, 0.334, 0.501, 0.668 or 0.835 mL) with 10-v mL calcium stock solution diluted to c=10, 20, 30, 40 or 50 mM concentration by TBS, respectively. Immediately after, 10 mL phosphate stock solution diluted to c/2 concentration was added to the PAH/calcium complex mixture without stirring. The suspensions were then centrifuged at 13000 rpm for 20 min, washed with ethanol, stored at −80° C. and freeze-dried at −4° C. for 24 h. The same procedure was used to prepare positively charged nanoparticles but here calcium solution (concentration=c/2) were added to a PAH/phosphate complex mixture. Control samples were also prepared using the same concentrations described above, but in the absence of the polymers.

Preparation of injectable compositions: The freeze dried hybrid nanoparticles were dispersed in Milli-Q water (20% w/v %) and sonicated for 20 minutes. The pastes containing oppositely charged hybrid nanoparticles were prepared by mixing of equal amounts of the PAH/CaP and PAA/CaP as-synthesized dispersions (solid content of ~0.03 w/v %).

Example 2

Large-Scale Production Using High Concentrations

For large-scale production of calcium phosphate, calcium and phosphate ions are used at higher concentrations, e.g. 100 mM and higher. However, increasing the ion concentration results in forming of larger particles with a broad size distribution and therefore alters their suitability for using in injectable formulations or solid structures. To address this problem, the synthesis procedure is modified so that the system is subjected to ultrasonication immediately after formation of the polymer-stabilized calcium phosphate hybrid particles. As an example, negatively charged hybrid nanoparticles were prepared by first mixing 50 mL of PAA solution (3 wt %) with 100 mL calcium solution (200 mM) followed by addition of 150 mL phosphate solution (100 mM) to the PAA/calcium complex mixture without stirring. The suspension was then subjected to ultrasonication using an ultrasonic homogenizer (Branson Sonifier S-450A) for 5 min and at 30% power output, centrifuged at 5000 rpm for 20 min, washed with ethanol, stored at −80° C. and freeze-dried at −4° C. for 24 h. Using ultrasonication for 5 min decreased the particle size and polydispersity index (PI) from ~700 nm and 0.5 to less than 300 nm and 0.25, respectively. The time, temperature, and power of the ultrasonication can be exploited to tune the particle size. The polydispersity index is a measure of the size distribution of the nanoparticles as determined by dynamic light scattering (DLS). It is the squared ratio of deviation from the mean size and the mean size (i.e., $(deviation/mean)^2$). For a perfectly uniform sample, it is 0; for monodisperse systems, it is <0.1, for systems with moderate dispersity, it is between 0.1 and 0.4, and for polydisperse systems, it is greater than 0.4.

Example 3

Injectable Paste of Polymer-ACaP:Silicate Nanosheet:Graphene Oxide

An optically transparent dispersion of silicate nanosheets, 10.0% (w/v), was prepared by mixing silicate nanosheets (SNs) with milli-Q water for 2 h, followed by ultrasonication using an ultrasonic homogenizer (Branson Sonifier S-450A), for 5 min. A homogeneous suspension of graphene oxide (GO) with a concentration of 2.0 mg mL$^{-1}$ was obtained by dispersing GO in milli-Q water, followed by sonication in a water bath for 90 min and ultrasonication using an ultrasonic homogenizer (Branson Sonifier S-450A), for 2 min. Then equal volumes of SNs and GO dispersions were mixed with the freeze-dried polymer/ACaP hybrid nanoparticles (PAH-CaP or a 50/50 mixture of PAH-CaP and PAA-CaP) to form a homogeneous paste with a composition of 100:100:2 (Polymer-ACaP:SNs:GO).

Example 4

Synthesis and Structural Characterization of Graphene-Silicate Nanosheet Materials Gelatin (type A, from porcine skin), from Sigma-Aldrich Co. LLC, silicate nanosheets (Laponite XLG, 25-30 nm in diameter and 1 nm thick) from BYK-Chemie GmbH, Wesel, Germany, and Milli-Q®, registered trademark owned by Merck KGaA, Germany, water were used. The materials were prepared by complexation of gelatin and Laponite in an aqueous solution followed by carbonization. A synthetic procedure may involve the preparation of a stock solution of 2 percent weight per unit volume, i.e., the weight in grams of solute per 100 mL of solution, (% (w/v)), gelatin by adding of gelatin powder to milli-Q water at 40° C. to form a mixture and then stirring the mixture for a pre-determined time period, such as 2 hrs. An optically transparent dispersion of Laponite nanosheets, 1.5% (w/v), was prepared by mixing Laponite with milli-Q water for 2 hrs., followed by ultrasonication using an ultrasonic homogenizer (i.e., a Branson Sonifier S-450A), for 3 mins. until the pH of Laponite dispersion is 9.8. The calculated volume of the gelatin solution and Laponite dispersion was placed into individual vials, then calculated milli-Q water was added to each vial to reach a final volume of 10 ml.

Gelatin/Laponite complexes were prepared by adding a designated amount of Laponite dispersion (pH 9.8) to gelatin solution (weight ratio of Laponite:gelatin=1:1; 1:2; 1:5; 1:10) and mixing at 250 rpm for 45 sec. The mixtures were cast in polyethylene dishes and stored at 4° C. overnight and then transferred to freezer −80° C. Gelatin/Laponite aerogels were prepared by freeze-drying at −4° C. for 48 h. The aerogels were then heated to 800° C. under a flowing nitrogen atmosphere at a rate of 10° C./min and carbonized at this temperature for 2 hrs. to obtain gelatin-derived carbon/Laponite hybrid aerogels (GL-scaffolds). GL-powders were prepared by then grinding the GL-scaffolds. The samples were denoted as C[GEL/L=X], where X represented the ratio of gelatin (GEL) and Laponite, and C indicates for carbonized.

The GL materials were characterized by transmission electron microscopy (TEM, FEI Tecnai F30 at an accelerating voltage of 200 kV), scanning electron microscopy (SEM, Nova NanoSEM 230, USA), Raman spectroscopy (Horiba LabRamHR Evolution) with the laser excitation at 633 nm, X-ray photoelectron spectroscopy (XPS, Kratos AXIS Nova). The non-carbonized gelatin/Laponite samples were also analyzed with the Thermogravimetric Analyzer (TGA) (TA Instruments, Q600 SDT Simultaneous DSC-TGA) with 10° C. min-1 heating rate in a 50 mL/min nitrogen flow.

GL-scaffolds were prepared as 8 mm$^3$/cube, disinfected with 70% ethanol, incubated in 0.1% gelatin for 1 h and dried before culturing as. MSC cells were infected with AdGFP for 24 h, trypsinized and re-suspended at the concentration of $2 \times 10^4$/μl. A total of 50 μl volume cell suspension was seeded onto each GL-scaffold and incubated for 2 h in the incubator, and then the GL-scaffolds were transferred into 24-well plates and cultured in complete DMEM.

Figure 10:
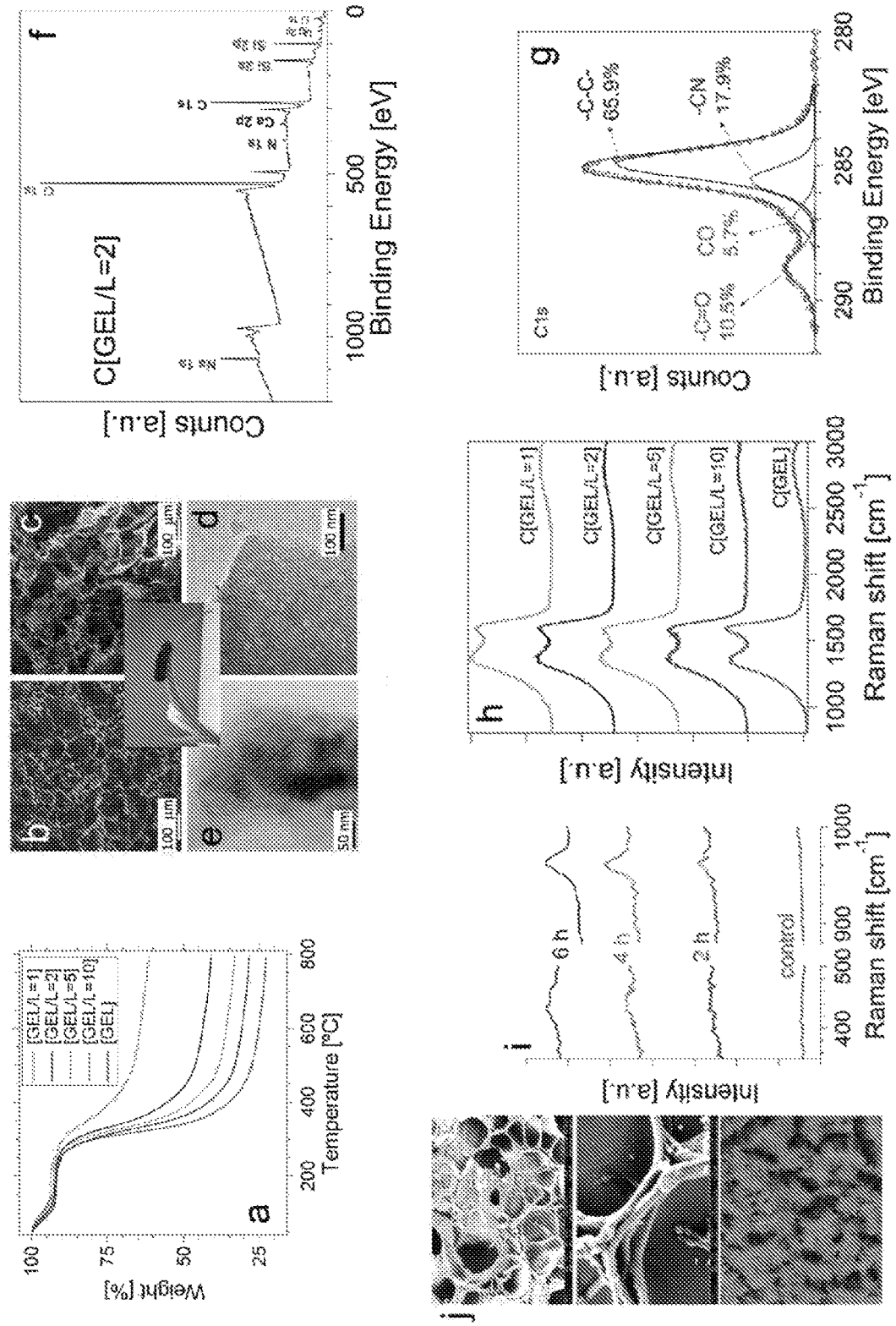
FIG. 10a shows curves of gelatin/Laponite materials.
FIGS. 10b and 10c are SEM images of gelatin/Laponite materials.
FIG. 10d is a TEM image of a gelatin/Laponite powder.
FIG. 10e shows a mesoporous structure of graphene-like layers in a gelatin/Laponite powder, where the inset shows a photograph of a scaffold standing on a spider plant.
FIG. 10f illustrates a X-ray photoelectron spectroscopy (XPS) survey spectrum of a graphene Laponite (GL) scaffold.
FIG. 10g shows XPS high-resolution spectrum of a GL scaffold.
FIG. 10h shows Raman spectra of GL-scaffolds with different compositions.
FIG. 10i shows Raman spectra showing the evolution of hydroxyapatite characteristic peaks on a GL scaffold immersed in 10x concentration simulated body fluid (SBF).
FIG. 10j shows SEM images showing the deposition of minerals on a GL-scaffold after 6 hrs. of immersion in 10xSBF.

Referring to FIG. 10, the structural characterization of gelatin (herein "GEL") derived graphene/Laponite materials is shown. Specifically, FIG. 10(a) shows thermogravimetric analyzer (TGA) curves of gelatin/Laponite, [GEL/L], materials under N$_2$ flux. FIG. 10(b) illustrates typical morphology of [GEL/L] materials. FIG. 10(c) shows a SEM image of a C[GEL/L=2] scaffold. FIG. 10(d) shows a transmission electron microscopy (TEM) image of c[GEL/L=2] powder, where the various arrows point to Laponite nanosheets. FIG. 10(e) shows a mesoporous structure of graphene-like layers in c[GEL/L=2] powder, where the inset shows a photograph of the c[GEL/L=2] scaffold standing on a spider plant. FIG. 10(f) illustrates a X-ray photoelectron spectroscopy (herein "XPS") survey spectrum of C[GEL/L=2] scaffold. FIG. 10(g) shows XPS C1s high-resolution spectrum of C[GEL/L=2]. FIG. 10(h) shows Raman spectra of GL-scaffolds with different compositions. FIG. 10(i) shows Raman spectra showing the evolution of hydroxyapatite characteristic peaks on C[GEL/L=2] scaffold immersed in 10× concentration SBF. FIG. 10(j) shows SEM images showing the deposition of minerals on a GL-scaffold after 6 hrs. of immersion in 10×SBF. Representative images of FIGS. 10(a)-(j) are shown.

Referring to the structural characterization of GL materials, the carbonization process and the composition of the obtained GL materials were assessed by thermogravimetric analysis (TGA) under N$_2$ flux. Specifically, carbonization appeared to be completed below 800° C. as shown in, for example, FIG. 10(a), confirming that the adopted experimental conditions were adequate for the preparation of GL materials. In the TGA results, the 6-8% weight loss up to 200° C. is attributed to dehydration and the weight losses at 300-750° C. are due to degradation of gelatin. No transformation of Laponite was observed below 800° C. Comparing with the decomposition profile of pure gelatin (referred to as "[GEL]" throughout FIG. 10), results show that complexation with Laponite nanosheets increases the thermal stability of the polymer. Quantitatively, almost 25% of the polymer has been converted into the carbonaceous material and incorporated into the GL materials. Therefore, the C[GEL/L=5] sample, for instance, consists of 57 wt % of carbonaceous material, and 43 wt % of Laponite nanosheets, referring to FIG. 10(a).

SEM images reveal a porous structure of the freeze-dried gelatin/Laponite materials before carbonization, as shown in, for example, FIG. 10(b), and preservation of the 3D porous structure following carbonization, as shown in, for example, FIG. 10(c). The size and distribution of pores within porous scaffolds plays an important role in their ability to infiltrate the cells and direct their distribution throughout the structure. Specifically, the GL materials displayed pore sizes between 50-100 μm, which remained nearly unchanged after carbonization. Further, transmission electron microscope (herein "TEM") images confirmed the uniform dispersion of Laponite nanosheets within the carbonaceous structure with no visible aggregates, as shown in, for example, FIG. 10(d). The TEM images also confirmed the 2D sheet-like structure of carbonaceous material in the form of nanoparticles and the presence of mesopores in their structure FIG. 10(e).

FIG. 10(f) shows X-ray photoelectron spectroscopy ("XPS") conducted to determine the elements and their chemical states in the GL materials. The survey spectrum of C[GEL/L=2] shows the presence of C (about 285 eV), O (about 531 eV), Si (about 100 and 150 eV) and other elements present in Laponite structure including Li, Ca, Mg and Na as shown in, for example, FIG. 10(f). The C1s spectrum was deconvoluted into four components as shown in FIG. 10(g). The strong peak at 284.8 eV is attributed to the graphitic (sp2 hybridized) carbon while the weak peaks at higher binding energies may be ascribed to the carbon combined with elements such as N and O with high electronegativity. Specifically, the peak at 285.6 eV is assigned to the carbons on the C—N bonds (remained from gelatin). Also shown in FIG. 10(g), the peaks at 286.9 eV and 288.9 eV correspond to the carbon from C—O bonds and C=O bonds, respectively. Quantitatively, approximately 66% of the carbonaceous material composed C—C bonds, which implies the relatively low defect of carbon in the GL hybrids and formation of graphene-like structures.

Formation of graphene was confirmed by Raman spectroscopy. The Raman spectrum of the GL hybrids showed the characteristic G-band (graphitic band) at (1580-1600 cm$^{-1}$) assigned to E$_{2g}$ vibrational mode, and a D-band (defect band) at (1330-1340 cm$^{-1}$) associated with the defect-activated breathing modes of A$_{1g}$ symmetry of aromatic rings, as shown in FIG. 10(h). These bands along with 2D-band (2500-2900 cm$^{-1}$) are well known to be indicative of graphene. The intensity ratio of I$_D$/I$_G$ of D and G bands provide information of disordered structure. The intensity ratio increased with increasing Laponite content in the GL materials and changed from 0.95 in the case of pure gelatin carbonized in the absence of Laponite, c[GEL], to 1.07 for C[GEL/L=1] sample. The higher I$_D$/I$_G$ ratios indicate increases in structural defects and bonding disorder potentially due to the existence of a large amount of pores and edges in the carbonaceous materials formed in the presence of Laponite nanosheets.

To evaluate the bone-bonding ability of the GL-scaffolds, in vitro biomineralization was analyzed by submerging the GL-scaffolds in SBM and following deposition of apatite-like deposits on their surfaces. Scanning electron microscopy (SEM) and Raman spectroscopy clearly showed the formation of hydroxyapatite (herein "HA") layer on the surface of C[GEL/L=2] after 6 hrs. of immersion in 10× concentration SBF, as shown in FIGS. 10(i)-(j). The evolution of vibrational bands at 430-450 cm$^{-1}$ and 970 cm$^{-1}$, corresponded to $v_2$ PO4$^{3-}$ and $v_1$ PO4$^{3-}$ domains of HA are shown FIG. 10(i).

Figure 11:
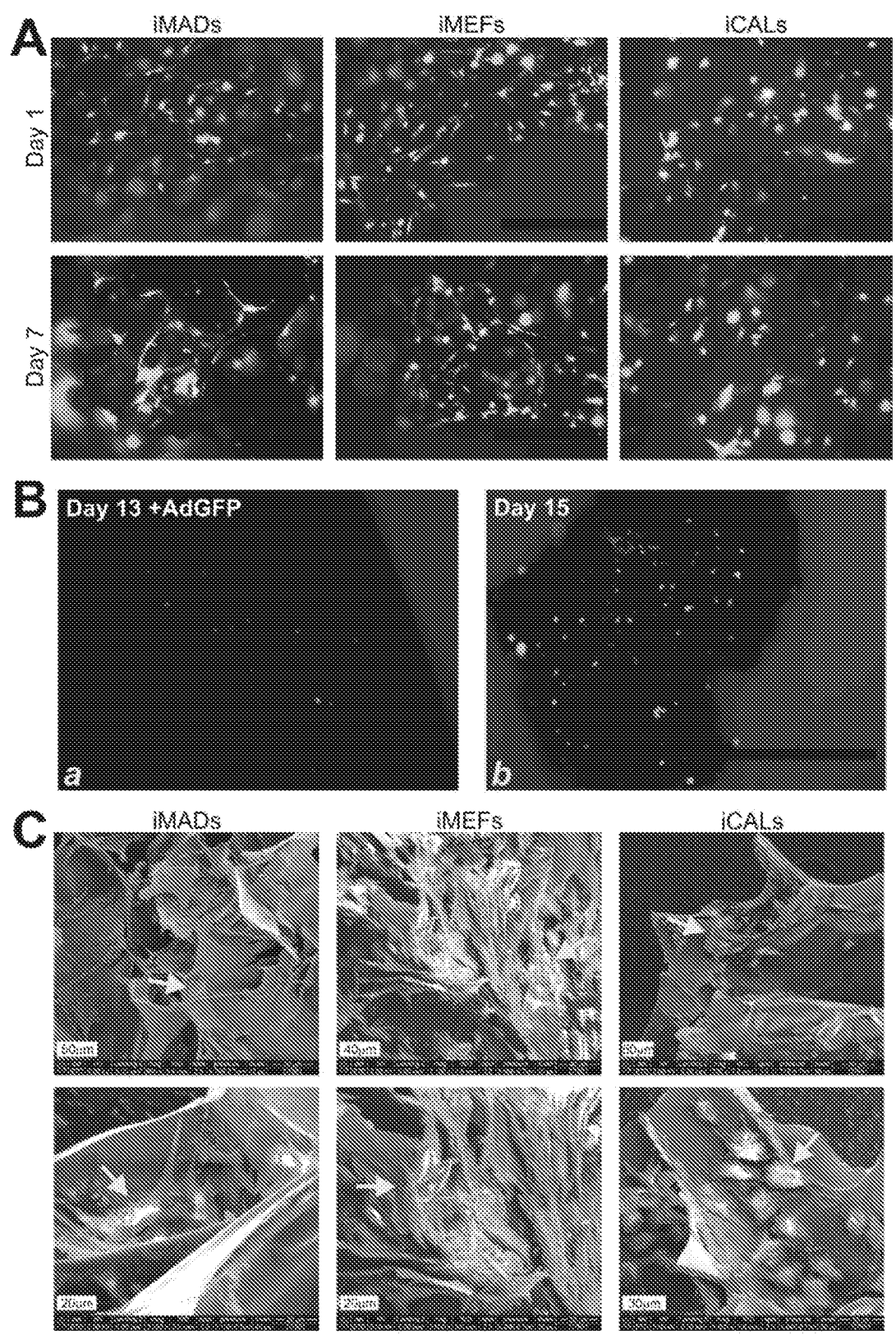
FIG. 11 shows images related to the attachment, proliferation and morphology of mesenchymal stem cells (MSCs) on GL-scaffolds.

Referring now to FIG. 11, images related to the attachment, proliferation and morphology of MSCs on the discussed GL-scaffolds are shown. FIG. 11A shows iMADs, iMEFs and iCALs (immortalized mouse calvarial cells), which exhibited a homogeneous attachment at day 1 and remained viable at day 7. FIG. 11B shows iMEFs, which maintained proliferative after 15 days. Specifically, FIG. 11B shows, at day 13, a second dose of AdGFP, which was added to the medium and also shows a GFP signal observed at day 15. FIG. 11C further illustrates iMADs, iMEFs and iCALs' morphology and interaction with the GL-scaffolds. Cells were fixed at day 7 for SEM imaging. MSCs were indicated by arrows. Representative images are shown.

Further, with regard to cell attachment, morphology and proliferation on the GL-Scaffold, the biocompatibility of the GL-scaffold (C[GEL/L=2]) was tested. Three MSC lines, iMADs, iMEFs and iCALs, were infected with AdGFP, and seeded on the surface of the scaffold. As shown in FIG. 11A, at day 1, a homogeneous attachment of cells on the scaffold was observed. Certain cells were clear in shape while others were not, indicating that cells may attach to, for example, the outer and inner faces of the scaffold. At day 7, all three lines were found viable, and cell proliferation was clearly observed, as shown in FIG. 11A. Upon continued culturing, the GFP signal dropped as cells proliferated and divided. For example, at day 13, when another dose of AdGFP was added to the medium, the cells were able to be re-infected as the GFP signal was re-intensified at day 15 as shown in, for example, FIG. 11B, indicating that the infected cells on the scaffold were still viable and maintained a high proliferative capability after more than two weeks of culture since adenoviruses primarily infect actively dividing cells. Cell morphology and interactions with the scaffold were confirmed by both microscopy. The iMADs and iMEFs had an elongated morphology while iCALs adapted a relatively round morphology. Additional morphological details were revealed by SEM as the MSC cells populated on both the outer and the inner face of the scaffold. Also, the iMADs had many long protrusions stretched out from the cell body that crossed the micro pores of the scaffold and attached to the nearby surface as shown in FIG. 11C.

Figure 12:
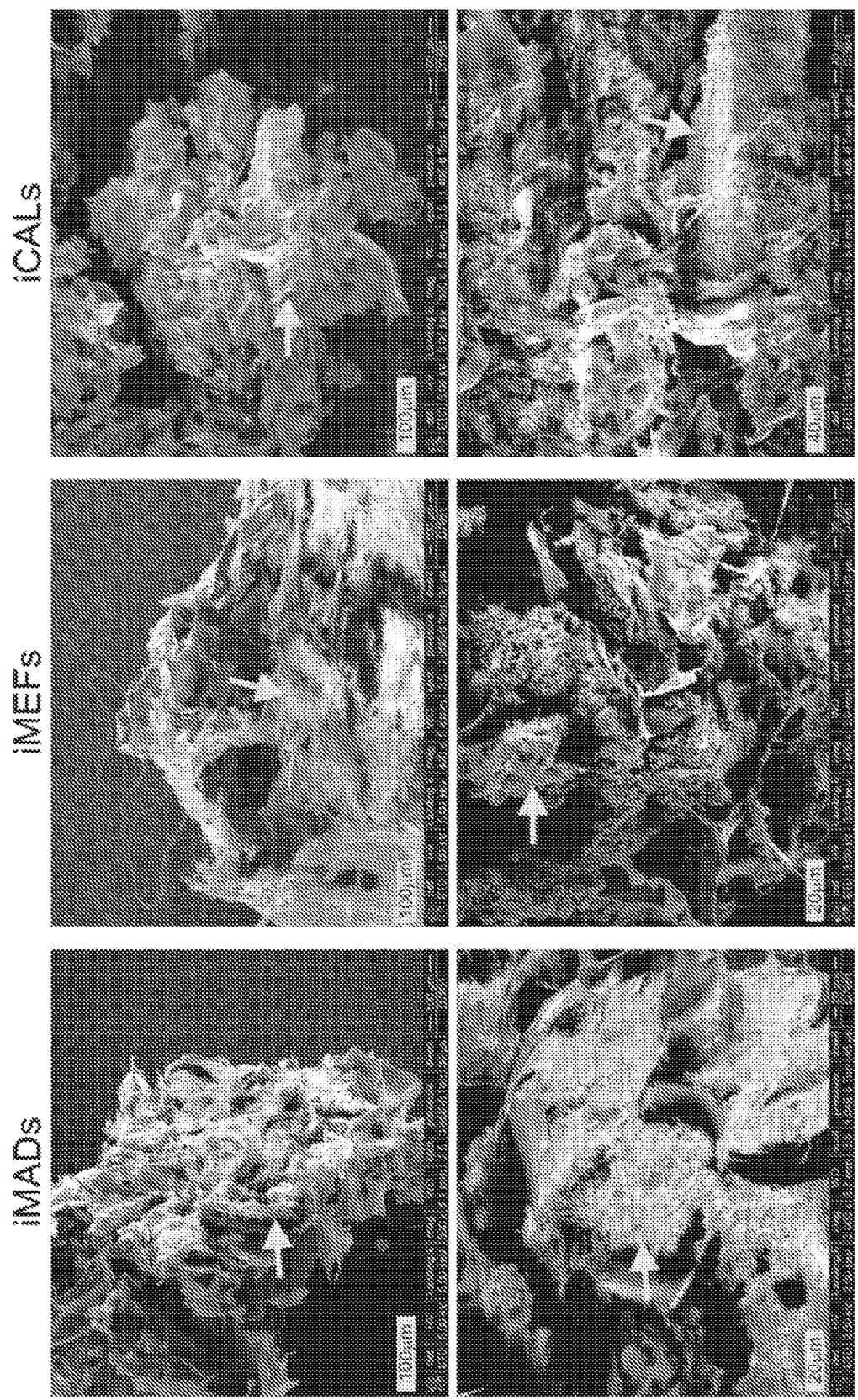
FIG. 12 shows images related to the effect of GL scaffolds on cell morphology and mineralization of MSCs.

Referring now to FIG. 12, the effect of GL-scaffolds on cell morphology and mineralization of MSCs is shown. In some embodiments, the MSCs were seeded on the scaffolds and cultured for 15 days in mineralization medium prior to SEM imaging. Well-mineralized matrix with many mineral nodules on the surface of the cells and scaffolds are indicated by arrows. Representative images are shown.

With regard to the induction of osteogenic differentiation of the MSCs and the enhancement of matrix mineralization by GL-Scaffold, MSCs-seeded scaffolds were cultured in mineralization medium, and SEM was performed at day 14. All three lines cultured on the scaffold were found to show numerous well-mineralized nodules with many mineral particles observed on the surface of the scaffold, as shown in FIG. 12.

Figure 13:
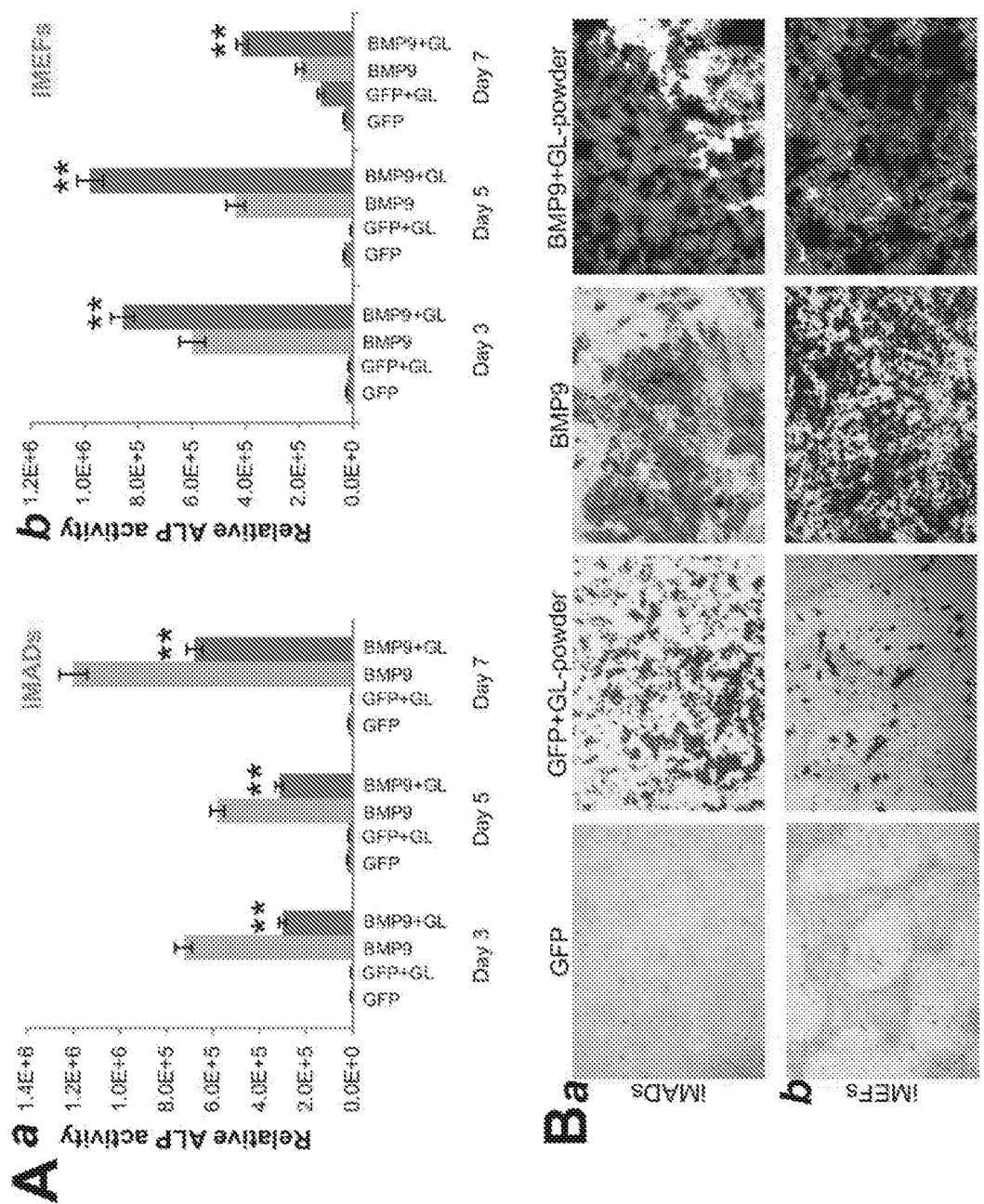
FIG. 13A shows graphs illustrating the effect of GL-powder on BMP9-induced alkaline phosphotase (ALP) activity of iMADS immortalized Mouse Adipose-Derived mesenchymal stem cells and immortalized Mouse Embryo Fibroblast (iMEF) mesenchymal stem cells.
FIG. 13B shows representative images showing the effect of GL-powder on ALP activity and matrix mineralization of MSCs.

Referring now to FIG. 13, the effect of GL-powder on alkaline phosphotase (ALP) activity and matrix mineralization of MSCs is shown. Specifically, FIG. 13A shows GL-powder decreases BMP9-induced ALP activity of iMADs (a), while enhances that of iMEFs (b). The cells were infected with AdGFP or AdBMP9, relative ALP activity was quantitatively determined at 3, 5, and 7 days after infection. Assays were done in triplicate. FIG. 13B shows that GL-powder promotes BMP9-induced matrix mineralization of both iMADs (a) and iMEFs (b). Cells were infected with AdGFP or AdBMP9, cultured in mineralization medium for 10 days and stained with Alizarin Red S. Assays were done in triplicate. Representative images are shown. For FIG. 13A, "*", p<0.05 when compared to BMP9 group; "*", p<0.05 when compared to GFP group.

Generally, FIG. 13 relates to the synergistic augmentation of BMP9-induced osteogenic differentiation of stem Cells by GL-Powder. For example, the osteoinductivity of the GL-powder in iMEFs and iMADs in the presence or absence of BMP9 stimulation was tested. In MSC lines, GL-powder alone induced negligible ALP activity while BMP9 alone induced robust ALP activities, as shown in FIG. 13A. When iMADs were infected with AdBMP9, the ALP activity was shown to decrease in the presence of GL-powder, as shown in FIG. 13B(a). Conversely, when cultured with AdBMP9, iMEFs' ALP activity was increased by the GL-powder at days 3, 5 and 7, as shown in FIG. 13B(b). This opposite effect of GL-powder on iMADs when compared to iMEFs may be due to the relative increased differentiation of iMADs cells relative to iMEFs, such that GL-powder treatment may further accelerate the BMP9-induced osteogenic differentiation process, leading to the decrease in the early osteogenic marker ALP activity. Further, Alizarin Red S staining showed that the GL-powder significantly promoted matrix mineralization in both iMADs and iMEFs when treated with AdBMP9, but failed to do so when AdBMP9 was absent, as shown in FIG. 13B(a)-(b). Thus, these results indicate that GL-powder may accelerate BMP9-induced terminal osteogenic differentiation of MSCs.

Figure 14:
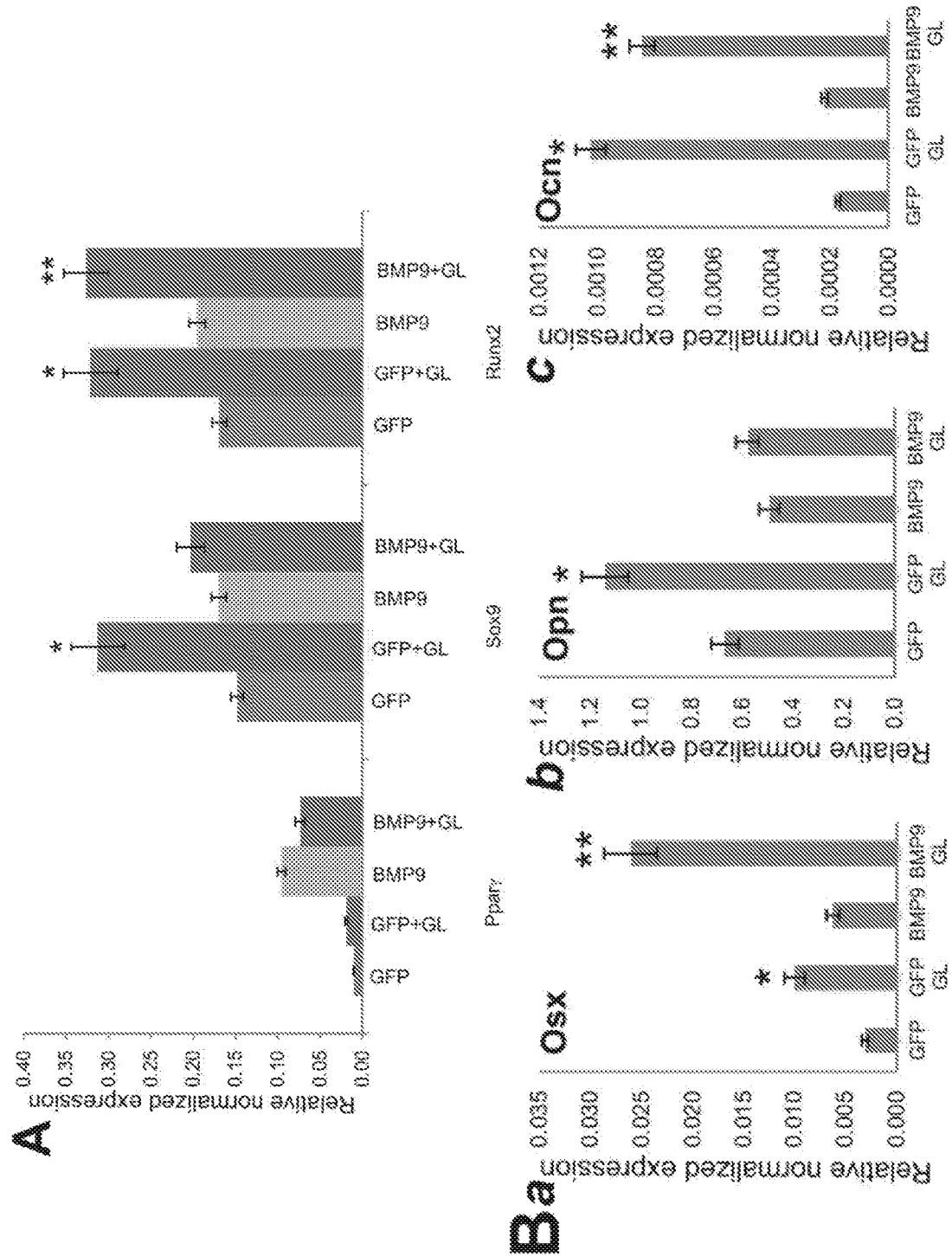
FIGS. 14A and 14B are graphs showing the effect of GL-powder on the expression of osteogenic markers.

Referring to FIG. 14, the effect of GL-powder on the expression of osteogenic markers is shown. Specifically, FIG. 14(A) shows that GL-powder up-regulates the expression of Sox9 and Runx-2 while has limited impact on PPARγ expression. Subconfluent iMADs cells were infected with AdGFP or AdBMP9, cultured with or without GL-powder. Total RNA was isolated at 48 h and subjected to TqPCR analysis using gene-specific primers for mouse Runx2, PPARγ and Sox9. FIG. 14(B) shows that GL-powder promotes the expression of osteogenic markers Osx, Ocn, and Opn. Subconfluent iMADs cells were infected with AdGFP or AdBMP9, cultured with or without GL-powder. Total RNA was isolated at 48 h and subjected to TqPCR analysis using gene-specific primers for mouse-derived Osx, Opn, and Ocn. GAPDH was used as a reference gene. Reactions were done in triplicate. "*", p<0.05 when compared to GFP group, "**", p<0.001 when compared to GFP group.

Since MSCs are able to differentiate into different lineages, the expression of the markers for osteogenic, chondrogenic and adipogenic lineages when cultured with the GL-powder were tested. The expression of chondrogenic and osteogenic markers Sox9 and Runx2, but not adipogenic marker PPARγ, was significantly increased by the GL-powder, as shown in FIG. 14A. Consistent with earlier observations, the induction of Runx2 expression was not apparent at 48 hrs. after AdBMP infection although AdBMP9 induced robust PPARγ expression. Furthermore, the expression of Runx2 downstream target gene Osterix was induced by GL-powder, which was potentiated in the presence of BMP9, as shown in FIG. 14B(a). Afterwards, bone markers Opn and Ocn were also significantly up-regulated by GL-powder independent of BMP9 stimulation FIG. 14B (b)-(c). When viewed collectively, the results shown in FIG. 14 may demonstrate that GL-powder can induce osteogenic differentiation to certain extent by itself and/or act synergistically to promote BMP9-induced osteogenic differentiation of MSCs.

Figure 15:
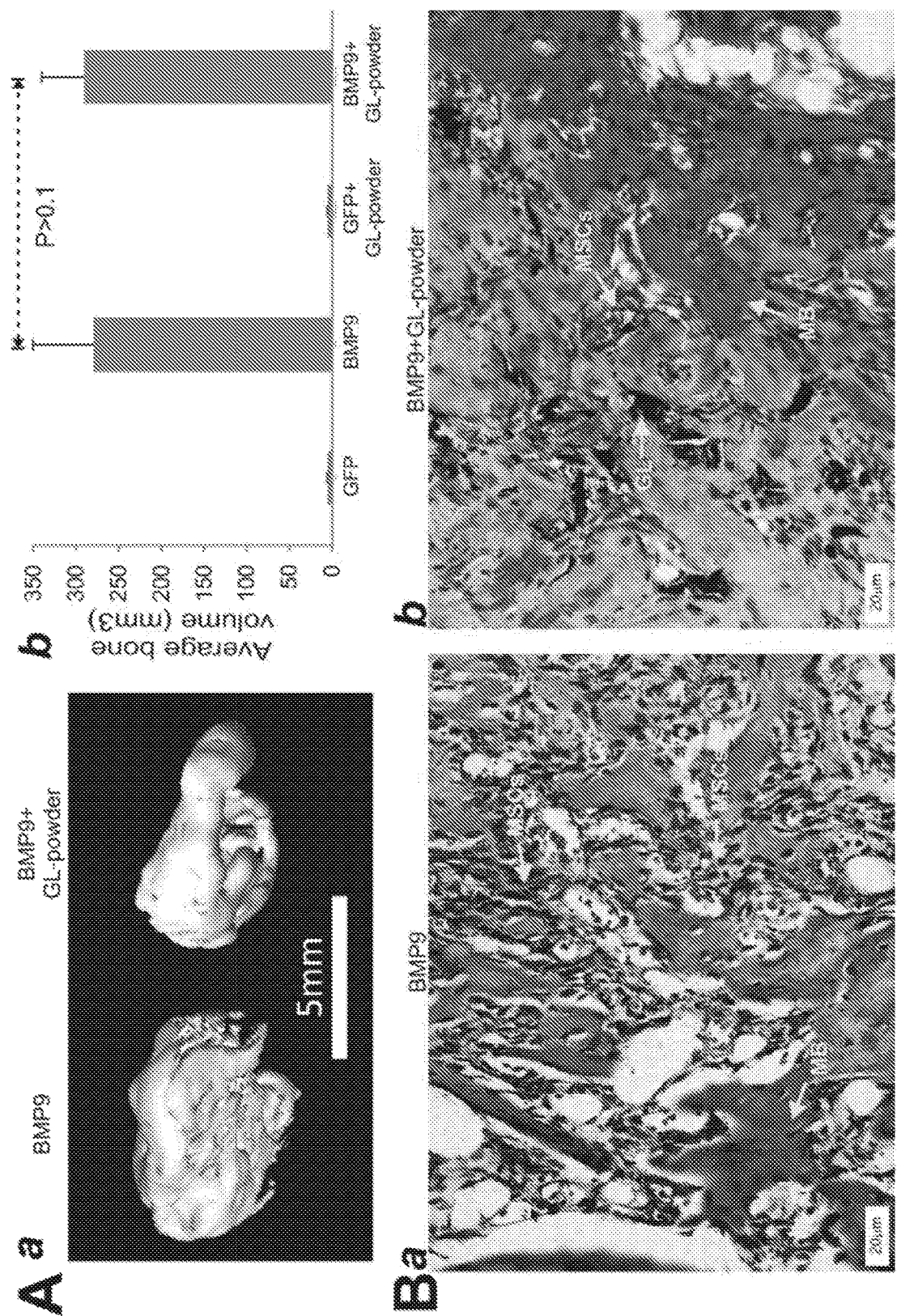
FIG. 15A shows comparative μCT imaging analysis of ectopic bone mass and a graph showing average bone volumes.
FIG. 15B shows images showing staining of the bone masses.

Referring now to FIG. 15, the augmentation of BMP9-induced ectopic bone formation by GL-Powder is shown. Specifically, FIG. 15A shows the μCT imaging analysis of ectopic bone masses. The retrieved bone masses from the iMEFs+BMP9 group and the iMEFs+BMP9+GL-powder group were imaged by μCT followed by 3D reconstruction, as shown in FIG. 15A(a). Representative images are shown. The average bone volumes for different groups were determined and analyzed by using the Amira program, as shown in FIG. 15(A)(b). FIG. 15B shows H & E staining of the retrieved bone masses. Representative images are shown.

The enhancement of BMP9-Induced ectopic bone formation and mineralization of bony masses by GL-powder was investigated further. Specifically, the effect of GL-powder on BMP9-induced ectopic ossification in an ectopic bone formation animal model was tested. When iMEFs were infected with AdBMP9 or AdGFP and mixed with or without GL-powder, the overall sizes were not found to differ significantly among the bony masses recovered from iMEFs+BMP9 and iMEFs+BMP9+GL-powder, as shown in FIG. 15A(a), while no detectable masses were retrieved from the AdGFP-transduced iMEFs only group and iMEFs+GL-powder group FIG. 15A(b). Histological evaluation revealed that consistent with our previous reports BMP9 induced robust bone formation of iMEFs although numerous yet-to-be differentiated MSCs were readily detectable, as shown in FIG. 15B(a). However, in the group of the BMP9-transduced iMEFs mixed GL-powder more robust trabecular bone structure and more mature bone, as shown in FIG. 15B(b), were found indicating that the inclusion of GL-powder with BMP9-transduced MSCs can lead to more robust bone formation in vivo, which was also mechanistically supported by in vitro studies.

The invention claimed is:

1. A composition comprising:
   a plurality of oppositely charged amorphous calcium phosphate hybrid nanospheres,
   wherein each calcium phosphate hybrid nanosphere comprises calcium phosphate and either an anionic organic polymer or a cationic organic polymer;
   a graphene-based material comprising graphene oxide; and
   a silicate nanosheet;
   wherein all of calcium phosphate hybrid nanospheres in the composition are amorphous.

2. The composition of claim 1, wherein the composition is lyophilized.

3. The composition of claim 1, wherein the composition comprises cationic organic polymers selected from at least one of poly (allylamine hydrochloride), poly (allylamine), poly (ethyleneimine), a poly (vinylpyridine) salt, poly (L-lysine), chitosan, gelatin, poly (diallyldimethylammonium chloride), and protamine.

4. The composition of claim 1, wherein the composition comprises anionic organic polymers selected from at least one of poly (aspartic acid), poly (styrenesulfonic acid) salts, poly (2-acrylamido-2-methylpropane sulfonic acid), deoxyribonucleic acid (DNA), carboxymethyl cellulose, amelogenin, osteopontin, sulfonated dextran, poly (glutamic acid), poly (vinylphosphonic acid) or poly (vinyl sulphonic acid).

5. The composition of claim 1, wherein the composition is an injectable paste.

6. The composition of claim 5, wherein the injectable paste contains approximately equal amounts of cationic organic polymers and anionic organic polymers.

7. The composition of claim 1, wherein the amount of calcium phosphate is between 25 wt % and 75 wt % of the composition and the amount of polymer is between 15 wt % and 65 wt % of the composition.

8. The composition of claim 6, wherein the anionic organic polymers comprise poly (acrylic acid) sodium salt and the cationic organic polymers comprise poly (allylamine hydrochloride).

9. The composition of claim 1, wherein the composition promotes osteogenic differentiation of mesenchymal stem cells in vitro and enhancing bone regeneration in vivo.

10. The composition of claim 1, wherein the composition exhibits self-healing properties.

11. The composition of claim 1, wherein the oppositely charged amorphous calcium phosphate hybrid nanospheres are electrostatically bound.

12. The composition of claim 5, wherein the oppositely charged amorphous calcium phosphate hybrid nanospheres are electrostatically self-assembled.

13. The composition of claim 5, wherein the composition comprises a 3D porous scaffold.

14. The composition of claim 5, wherein the injectable paste is self-setting.

* * * * *